US012623067B2

(12) United States Patent
Asirvatham et al.

(10) Patent No.: US 12,623,067 B2
(45) **Date of Patent: \*May 12, 2026**

(54) ELECTROPORATION DELIVERY SYSTEMS AND METHODS OF USING ELECTROPORATION DELIVERY SYSTEMS

(71) Applicants: Cardiac Pacemakers, Inc., St. Paul, MN (US); Mayo Foundation for Medical Education and Research, Rochester, MN (US)

(72) Inventors: Samuel J. Asirvatham, Rochester, MN (US); Suraj Kapa, Rochester, MN (US); Sarah M. Gruba, Vadnais Heights, MN (US); Douglas D. Pagoria, Forest Lake, MN (US); James P. Rohl, Prescott, WI (US); Chance M. Witt, Rochester, MN (US); Ammar M. Killu, Rochester, MN (US); Niyada Naksuk, Rochester, MN (US)

(73) Assignees: Cardiac Pacemakers, Inc., St. Paul, MN (US); Mayo Foundation for Medical Education and Research, Rochester, MN (US)

( * ) Notice: Subject to any disclaimer, the term of this patent is extended or adjusted under 35 U.S.C. 154(b) by 1011 days.

This patent is subject to a terminal disclaimer.

(21) Appl. No.: 17/833,269

(22) Filed: Jun. 6, 2022

(65) Prior Publication Data

US 2022/0296881 A1 Sep. 22, 2022

Related U.S. Application Data

(63) Continuation of application No. 16/107,046, filed on Aug. 21, 2018, now Pat. No. 11,389,642.

(Continued)

(51) Int. Cl.
*A61B 18/14* (2006.01)
*A61B 5/00* (2006.01)
(Continued)

(52) U.S. Cl.
CPC .............. *A61N 1/0412* (2013.01); *A61B 5/00* (2013.01); *A61B 5/366* (2021.01);
(Continued)

(58) Field of Classification Search
CPC ...... A61B 18/1492; A61B 2018/00351; A61B 2018/00577; A61B 2018/00613;
(Continued)

(56) References Cited

U.S. PATENT DOCUMENTS

2003/0204161 A1\* 10/2003 Ferek-Petric .......... A61N 1/325
604/20
2007/0129761 A1 6/2007 Demarais et al.
(Continued)

FOREIGN PATENT DOCUMENTS

WO WO 2017024123 2/2017
WO WO 2017123981 7/2017

OTHER PUBLICATIONS

Deodhar, A., et al., "Irreversible electroporation near the heart: Ventricular arrhythmias can be with ECG synchronization", Vascular and Interventional Radiology AJR:196(3): 1-16 (2011).
(Continued)

*Primary Examiner* — Michael F Peffley
*Assistant Examiner* — Amanda L Zink
(74) *Attorney, Agent, or Firm* — Fish & Richardson P.C.

(57) ABSTRACT

The present disclosure relates generally to electroporation systems and utilizing algorithms for electroporation pulse delivery including a patient's EKG/EGM monitoring. In some embodiments, an electroporation delivery system may include an electrocardiogram operatively connected to a
(Continued)

processing device and a memory. One or more sensors may be operatively connected to the electrocardiogram for measuring electrical activity QRS complex of a patient's heart. One or more electrodes for treatment may be disposed in, at, or near the patient's heart, the one or more electrodes operatively connected to a pulse delivery mechanism. The electroporation delivery system may be configured to determine whether an electroporation pulse is deliverable to a patient based on the electrocardiogram.

20 Claims, 15 Drawing Sheets

Related U.S. Application Data

(60) Provisional application No. 62/549,631, filed on Aug. 24, 2017.

(51) Int. Cl.

| | |
|---|---|
| *A61B 5/366* | (2021.01) |
| *A61N 1/04* | (2006.01) |
| *A61N 1/32* | (2006.01) |
| *A61B 5/361* | (2021.01) |
| *A61B 18/00* | (2006.01) |
| *A61N 1/08* | (2006.01) |
| *A61N 1/37* | (2006.01) |

(52) U.S. Cl.
CPC ........ *A61B 18/1492* (2013.01); *A61N 1/0476* (2013.01); *A61N 1/327* (2013.01); *A61B 5/361* (2021.01); *A61B 5/686* (2013.01); *A61B*
*2018/00351* (2013.01); *A61B 2018/00577* (2013.01); *A61B 2018/00613* (2013.01); *A61B 2018/00642* (2013.01); *A61B 2018/00702* (2013.01); *A61N 1/08* (2013.01); *A61N 1/3702* (2013.01)

(58) Field of Classification Search
CPC .......... A61B 2018/00642; A61B 2018/00702; A61B 5/00; A61B 5/361; A61B 5/366; A61B 5/686

See application file for complete search history.

(56) References Cited

U.S. PATENT DOCUMENTS

| | | | | |
|---|---|---|---|---|
| 2017/0035499 | A1* | 2/2017 | Stewart | A61B 18/1492 |
| 2018/0214195 | A1* | 8/2018 | Fraasch | A61N 1/303 |
| 2021/0338302 | A1* | 11/2021 | Paré | A61N 1/056 |
| 2023/0082389 | A1* | 3/2023 | Waldstreicher | A61N 1/06 607/50 |
| 2025/0261991 | A1* | 8/2025 | O'Brien | A61B 18/1492 |

OTHER PUBLICATIONS

International Preliminary Report on Patentability for the International Patent Application No. PCT /US2018/047264, dated Mar. 5, 2020, 10 pages.

International Search Report and Written Opinion for application No. PCT/US2018/047264, mailed on Feb. 6, 2019, 15 pages.

Extended European Search Report in EP Appln. No. 25217951.0, mailed on Feb. 20, 2026, 7 pages.

* cited by examiner

ELECTROPORATION DELIVERY SYSTEMS AND METHODS OF USING ELECTROPORATION DELIVERY SYSTEMS

CROSS-REFERENCE TO RELATED APPLICATIONS

This application is a continuation of U.S. application Ser. No. 16/107,046 filed Aug. 21, 2018 (now U.S. Pat. No. 11,389,642), which is a non-provisional application of, and claims the benefit of priority to, U.S. Provisional Application Ser. No. 62/549,631 filed Aug. 24, 2017, entitled "Electroporation Delivery Systems and Methods of Using Electroporation Delivery Systems." The entirety of the related applications are hereby expressly incorporated by reference herein.

FIELD

The present disclosure relates generally to electroporation systems, including reversible electroporation (RE) and irreversible electroporation (IRE) systems and methods for using electroporation systems and, more particularly, to utilizing algorithms for electroporation pulse delivery including a patient's EKG/EGM monitoring.

BACKGROUND

Reversible electroporation (RE) may be typically used for drug delivery to a selected tissue area by applying direct-current through electrodes. Irreversible electroporation (IRE) is typically used as a soft tissue ablation technique (e.g., tumor removal) by delivering direct-current energy in short pulses to the selected tissue. For patients with healthy heart rhythms, undergoing an electroporation procedure near the heart is generally acceptable, as the electroporation procedure may rely on an algorithm that utilizes the QRS complex to determine when a pulse is delivered to the patient (FIG. 1A). However, in a patient having an arrhythmia, for example, the Q wave, R wave, and/or the S wave may be uneven and irregular (e.g., a patient's heart rate may be irregular and/or faster than normal heart rates) (FIG. 1B). The algorithms currently utilized in electroporation systems do not take into account irregular QRS wave patterns, which could result in an electroporation pulse being delivered that may affect the QRS wave.

For example, when an electroporation pulse is delivered at less than or equal to 1.7 cm from the heart, a patient may experience a fatal (major) event. Even when an electroporation pulse is delivered at a distance greater than 1.7 cm from the heart, a patient may experience a minor event. Known algorithms typically issue a pulse within a certain time frame after the R wave. As can be seen in FIG. 1A, an electroporation pulse signal sent during an R wave in a regular heartbeat may be delivered prior to the T wave in the refractory period, while FIG. 1B illustrates that an irregular heartbeat may have a wider R wave, thereby resulting in a pulse occurring during the T wave. If an electroporation pulse is delivered during the T wave, a patient may experience malignant atrial and ventricular arrhythmias. In some instances, up to 14% of electroporation cases may cause ventricular fibrillation.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, an electroporation delivery system may include an electrocardiogram operatively connected to a processing device and a memory, one or more sensors operatively connected to the electrocardiogram for measuring electrical activity QRS complex of a patient's heart, and one or more electrodes for treatment at, in, or near the patient's heart, the one or more electrodes operatively connected to a pulse delivery mechanism. The electroporation delivery system may be configured to determine whether an electroporation pulse is deliverable to a patient based on the electrocardiogram.

According to an exemplary embodiment of the present disclosure, a method for delivering an electroporation pulse by an electroporation delivery system for treatment in, at, or near a patient's heart may include measuring electrical activity QRS complex of the patient's heart by an electrocardiogram and one or more sensors operatively connected to a processing device and a memory, calculating by the processing device a rolling average by averaging a series of four pulse parameters, comparing the rolling average to a determined value, and delivering an electroporation pulse by one or more electrodes operatively connected to a pulse delivery mechanism of the electroporation delivery system in response to the rolling average being equal to the determined value.

According to an exemplary embodiment of the present disclosure, a system for delivering an electroporation pulse by an electroporation delivery system for treatment in, at, or near a patient's heart may be configured to execute steps that include measuring electrical activity QRS complex of the patient's heart by an electrocardiogram and one or more sensors operatively connected to a processing device and a memory, calculating by the processing device a rolling average by averaging a series of four pulse parameters, comparing the rolling average to a determined value, and delivering an electroporation pulse by one or more electrodes operatively connected to a pulse delivery mechanism of the electroporation delivery system in response to the rolling average being equal to the determined value.

In various of the foregoing and other embodiments of the present disclosure the processing device may be configured to execute the following steps including measuring and averaging approximately 30 initial heartbeat durations of the patient's heart, calculating a rolling average by averaging a series of four heartbeat durations, and comparing the rolling average to the averaged initial heartbeat durations including a standard deviation. If the rolling average is equal to the average initial heartbeat durations within the standard deviation, the electroporation delivery system may deliver the electroporation pulse during a fifth heartbeat duration following the averaged series of four heartbeat durations, and if the rolling average is not equal to the average initial heartbeat durations within the standard deviation, the electroporation delivery system may not delivery the electroporation pulse during the fifth heartbeat duration following the averaged series of four heartbeat durations.

In various of the foregoing and other embodiments of the present disclosure the processing device may be configured to execute the following steps: (a) calculating a rolling average by averaging a series of four heartbeat durations, (b) setting the rolling average to a heartbeat average including a standard deviation, and (c) comparing the rolling average to a fifth heartbeat duration following the averaged series of four heartbeat durations. If the fifth heartbeat duration following the averaged series of four heartbeat durations is equal to the rolling average within the standard deviation, the electroporation delivery system may deliver the electroporation pulse during a sixth heartbeat duration following the fifth heartbeat duration, and if the fifth heartbeat duration following the averaged series of the four heartbeat durations is not equal to the rolling average within the standard deviation, the electroporation delivery system may not deliver the electroporation pulse during the sixth heartbeat duration following the fifth heartbeat duration. The steps (a)-(c) may be repeatable until at least one of: (i) delivery of electroporation pulses is complete; and (ii) after a predetermined number of electroporation pulses are not delivered during the following fifth or sixth heartbeat duration, the electroporation delivery system is stopped. Delivery of the electroporation pulse during the sixth heartbeat duration may occur at a time determined by the averaged series of four heartbeat durations divided by two after a Q wave of the QRS complex of the sixth heartbeat duration.

In various of the foregoing and other embodiments of the present disclosure the processing device may be configured to execute the following steps including measuring and averaging approximately 30 initial R wave amplitudes in the QRS complex of the patient's heart, calculating a rolling average by averaging a series of four R wave amplitudes, and comparing the rolling average to the average initial R wave amplitudes including a standard deviation. If the rolling average is equal to the average initial R wave amplitudes within the standard deviation, the electroporation delivery system may deliver the electroporation pulse during a fifth heartbeat duration following the averaged series of four R wave amplitudes. If the rolling average is not equal to the average initial R wave amplitudes within the standard deviation, the electroporation delivery system may not deliver the electroporation pulse during the fifth heartbeat duration following the averaged series of four R wave amplitudes.

In various of the foregoing and other embodiments of the present disclosure, the processing device may be configured to execute the following steps including calculating a rolling average by averaging a series of four R wave amplitudes in the QRS complex of the patient's heart, setting the rolling average to the averaged R wave amplitudes including a standard deviation, and comparing the rolling average to a fifth R wave amplitude of a fifth heartbeat duration following the averaged series of four R wave amplitudes. If the fifth R wave amplitude following the averaged series of four R wave amplitudes is equal to the rolling average within the standard deviation, the electroporation delivery system may deliver the electroporation pulse during a sixth heartbeat duration following the fifth R wave amplitude. If the fifth R wave amplitude following the averaged series of the four R wave amplitudes is not equal to the rolling average within the standard deviation, the electroporation delivery system may not deliver the electroporation pulse during the sixth heartbeat duration following the fifth R wave amplitude.

In various of the foregoing and other embodiments of the present disclosure, the electroporation delivery system may be configured for at least one of ablation and drug delivery. The electroporation pulse may be deliverable by the electroporation delivery system within 50 ms of the R wave of the fifth heartbeat duration. The electroporation pulse may be deliverable by the electroporation delivery system after 50 ms if an average distance between an S wave and a T wave of the QRS complex is greater than 50 ms plus two additional electroporation pulse durations.

In various of the foregoing and other embodiments of the present disclosure, the electroporation delivery may include one or more signal filters for extracting at least one of an R wave and a T wave of the QRS complex. The electroporation pulse may be deliverable in response to a positive value of the R wave and a negative value of the T wave output from the one or more filters. The electroporation pulse may not deliverable in response to a positive value of the R wave and a positive value of the T wave output from the one or more filters. The electroporation pulse may be deliverable in response to the R wave being within 70 ms and the negative value of the T wave output from the one or more filters. The electroporation pulse shape may be at least one of square-shaped and defibrillation-like shaped. The electroporation pulse shape may be at least one of monopolar and bipolar. The electroporation delivery system may be operational for treating at least one of atrial fibrillation and cancer disposed in, at, or near the heart.

In various of the foregoing and other embodiments of the present disclosure, systems and methods may include that pacing of the patient's heart may be adjustable for electroporation pulse delivery by induced pacing, including the following steps including pacing a portion of the patient's heart, detecting an evoked potential, wherein if no evoked potential is detected, the pacing of the portion of the patient's heart may be continued and no electroporation pulse may be delivered, and in response to detecting evoked potential, determining if the detection occurs during a vulnerable period of a T wave, wherein in response to the detection occurring during the vulnerable period of the T wave, the pacing of the portion of the patient's heart may be continued and no electroporation pulse may be delivered, and wherein in response to the detection not occurring during the vulnerable period of the T wave, the electroporation pulse may be delivered. Pacing of the patient's heart may be adjustable for electroporation pulse delivery by at least continuous pacing, including the following steps including (a) sending a continuous pacing signal to the patient's heart to maintain the heart in a contracted state, (b) during the continuous pacing, delivering one or more electroporation pulses, and (c) monitoring heart rhythms of the patient for irregularities, wherein in response to detecting an irregularity, pacing the patient's heart to a normal rhythm; and wherein in response to detecting a regular heartbeat, steps (a), (b), and (c) may be repeated if additional treatment is needed. Pacing of the patient's heart may be adjustable for electroporation pulse delivery by at least administering a drug dosage for adjusting the pace of the patient's heart. Electroporation pulse delivery may be paused for monitoring the electrocardiogram for heart rhythms.

In various of the foregoing and other embodiments of the present disclosure, systems and methods may include that the processing device may be configured to execute the following steps including measuring and averaging approximately 30 initial heartbeat durations of the patient's heart, calculating a rolling average by averaging a series of four heartbeat durations, and comparing the rolling average to the averaged initial heartbeat durations including a standard deviation. If the rolling average is equal to the average initial heartbeat durations within the standard deviation, the electroporation pulse may be deliverable during a fifth heartbeat duration following the averaged series of four heartbeat durations. If the rolling average is not equal to the average initial heartbeat durations within the standard deviation, the electroporation pulse may not be deliverable during the fifth heartbeat duration following the averaged series of four heartbeat durations.

In various of the foregoing and other embodiments of the present disclosure, systems and methods may include that the processing device may be configured to execute the following steps including calculating a rolling average by averaging a series of four heartbeat durations, setting the rolling average to a heartbeat average including a standard deviation, and comparing the rolling average to a fifth heartbeat duration following the averaged series of four heartbeat durations. If the fifth heartbeat duration following the averaged series of four heartbeat durations is equal to the rolling average within the standard deviation, an electroporation pulse may be deliverable during a sixth heartbeat duration following the fifth heartbeat duration. If the fifth heartbeat duration following the averaged series of the four heartbeat durations is not equal to the rolling average within the standard deviation, the electroporation pulse may not be deliverable during the sixth heartbeat duration following the fifth heartbeat duration. Delivery of the electroporation pulse during the sixth heartbeat duration may occur at a time determined by the averaged series of four heartbeat durations divided by two after a Q wave of the QRS complex of the sixth heartbeat duration.

In various of the foregoing and other embodiments of the present disclosure, systems and methods may include that the processing device may be configured to execute the following steps including measuring and averaging approximately 30 initial R wave amplitudes in the QRS complex of the patient's heart, calculating a rolling average by averaging a series of four R wave amplitudes, and comparing the rolling average to the average initial R wave amplitudes including a standard deviation. If the rolling average is equal to the average initial R wave amplitudes within the standard deviation, the electroporation pulse may be deliverable during a fifth heartbeat duration following the averaged series of four R wave amplitudes. If the rolling average is not equal to the average initial R wave amplitudes within the standard deviation, the electroporation pulse may not be deliverable during the fifth heartbeat duration following the averaged series of four R wave amplitudes.

In various of the foregoing and other embodiments of the present disclosure, systems and methods may include that the processing device may be configured to execute the following steps including calculating a rolling average by averaging a series of four R wave amplitudes in the QRS complex of the patient's heart, setting the rolling average to the averaged R wave amplitudes including a standard deviation, and comparing the rolling average to a fifth R wave amplitude of a fifth heartbeat duration following the averaged series of four R wave amplitudes. If the fifth R wave amplitude following the averaged series of four R wave amplitudes is equal to the rolling average within the standard deviation, the electroporation pulse may be deliverable during a sixth heartbeat duration following the fifth R wave amplitude. If the fifth R wave amplitude following the averaged series of the four R wave amplitudes is not equal to the rolling average within the standard deviation, the electroporation pulse may not be deliverable during the sixth heartbeat duration following the fifth R wave amplitude.

In various of the foregoing and other embodiments of the present disclosure, systems and methods may include one or more signal filters for extracting at least one of an R wave and a T wave of the QRS complex. The electroporation pulse may be deliverable in response to a positive value of the R wave and a negative value of the T wave output from the one or more filters. The electroporation pulse may not be deliverable in response to the positive value of the R wave and a positive value of the T wave output from the one or more filters. The electroporation pulse may be deliverable in response to the R wave being within 70 ms and the negative value of the T wave output from the one or more filters.

In various of the foregoing and other embodiments of the present disclosure, systems and methods may include that pacing of the patient's heart may be adjustable for electroporation pulse delivery by induced pacing, including the following steps including pacing a portion of the patient's heart, detecting an evoked potential, wherein if no evoked potential is detected, the pacing of the portion of the patient's heart may be continued and no electroporation pulse may be delivered, and in response to detecting evoked potential, determining if the detection occurs during a vulnerable period of a T wave. In response to the detection occurring during the vulnerable period of the T wave, the pacing of the portion of the patient's heart may be continued and no electroporation pulse may be delivered. In response to the detection not occurring during the vulnerable period of the T wave, the electroporation pulse may be delivered. Pacing of the patient's heart may be adjustable for electroporation pulse delivery by continuous pacing, including the following steps including (a) sending a continuous pacing signal to the patient's heart to maintain the heart in a contracted state, (b) during the continuous pacing, delivering one or more electroporation pulses, and (c) monitoring heart rhythms of the patient for irregularities. In response to detecting an irregularity, the patient's heart may be paced to a normal rhythm, and in response to detecting a regular heartbeat, steps (a), (b), and (c) may be repeated if additional treatment is needed. Electroporation pulse delivery may be paused for monitoring the electrocardiogram for regular heart rhythms. An electroporation pulse shape may be at least one of square-shaped and defibrillation-like shaped. The electroporation pulse shape may be at least one of monopolar and bipolar. The electroporation delivery system may be operational for treating at least one of atrial fibrillation and cancer disposed in, at, or near the heart.

In various of the foregoing and other embodiments of the present disclosure, systems and methods may include that the determined value may be a fifth heartbeat parameter following the averaged series of four heartbeat parameters, and the rolling average may be set to a heartbeat average including a standard deviation. In each of the foregoing and other embodiments of the present disclosure, systems and methods may further comprise delivering the electroporation pulse during a fifth heartbeat duration following the averaged series of four heartbeat parameters, and not delivering the electroporation pulse during the fifth heartbeat duration following the averaged series of four heartbeat parameters in response to the rolling average not equaling the determined value. In each of the foregoing and other embodiments of the present disclosure, systems and methods may further comprise delivering the electroporation pulse during a sixth heartbeat duration following a fifth heartbeat duration, and not delivering the electroporation pulse during the sixth heartbeat duration following the fifth heartbeat duration in response to the fifth heartbeat parameter not equaling the rolling average within the standard deviation. A heartbeat parameter may be at least one of a heartbeat duration and an R wave amplitude. In each of the foregoing and other embodiments of the present disclosure, systems and methods may further comprise adjusting a pace of the patient's heart at least one of before, during, and after delivering the electroporation pulse.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

One challenge with using a running template of QRS morphology may be when a heart rhythm has changed to an arrhythmia prior to starting the count for which electroporation may be delivered. The QRS morphology may change significantly as energy is delivered, although it may not be disadvantageous and may not even necessitate stoppage of energy delivery. One possible way to get around this is incorporation of an existing template that is annotated by a user stating template 1—normal (e.g., FIG. 1A) and template 2—targeted arrhythmia (e.g., FIG. 1B). If the QRS complex stays in template 1, then energy may continue to be delivered. If the QRS complex transitions from template 2 to template 1, then energy may continue to be delivered. However, if any change to a QRS other than template 1 or 2 is seen, then energy delivery may be stopped because the patient may be experiencing a pro-arrhythmia, or a reference point may no longer be reliable for timing of energy delivery.

Figure 1B:
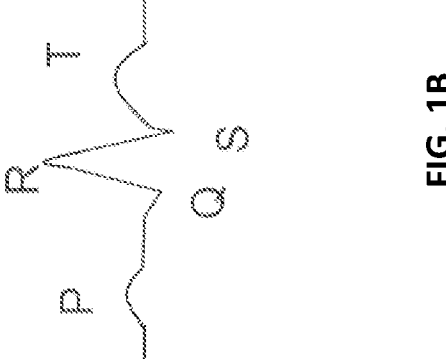
FIG. 1B illustrates an irregular QRS complex wave of an unhealthy heart.

As mentioned above with respect to FIG. 1A, the QRS complex illustrates a heart rate signal seen in a typical electrocardiogram (EGM, EKG) of a healthy patient (e.g., a normal heart rhythm). By issuing an electroporation pulse to occur during the absolute refractory period, for example, between the S wave and the T wave, external stimuli are incapable of inducing action potential, thereby preventing malignant arrhythmias. In some embodiments, an electroporation pulse may include a reversible electroporation (RE) pulse, and an irreversible electroporation (IRE) pulse. Additionally, an electroporation pulse may be one or more square wave pulses delivered during the refractory period, between each heartbeat. An algorithm may generate a pulse 50 ms after the Q wave. However, when a patient has an irregular heartbeat signal (e.g., an abnormal or irregular heart rhythm), as illustrated in FIG. 1B, a pulse generated 50 ms after the Q wave may occur during the T wave and potentially increase a patient's risk of injury. To account for irregular heartbeats, an algorithm may instead be used that includes a rolling average of a patient's electrocardiogram to determine when to send an electroporation pulse. Exemplary embodiments of algorithms in accordance with the present disclosure may be used with an internal electrocardiogram (e.g., via at least one of a coronary sinus (CS) catheter, pacemaker, and electroporation device, such as a reversible (RE) or irreversible (IRE) device) and/or a 3-lead, 12-lead, or a modified 12-lead external electrocardiogram.

The systems and methods described herein are intended to overcome the disadvantages in existing electroporation delivery systems by monitoring EKG, EGM wave signals and only delivering a pulse if selected conditions are satisfied. If the selected conditions have not been met than the electroporation delivery system will not send a pulse signal. This helps to ensure patient safety, in particular for patients with arrhythmias or other heart conditions that may result in an irregular heart rate. As mentioned above, if a pulse is to be delivered at, in, and/or near the heart (where "near the heart" may be less than or equal to 1.7 cm from the heart), an electroporation pulse being delivered at an incorrect portion of the EKG/EGM signal may be fatal in a patient. So that an electroporation delivery system may be used for treatment in humans, pulse delivery triggering algorithms are needed to provide a safe and reliable delivery method. For example, treatment may include energy delivery for ablation of tumors or other malignancies in IRE delivery systems, and/or drug delivery in RE delivery systems. Including an electroporation pulse delivery algorithm, such as the algorithms described herein, is not intended to limit the electroporation delivery system's ability to cause energy delivery in the selected area of the patient but to restrict undesirable energy delivery at selected points of the QRS wave complex. For example, an electroporation delivery system utilizing a delivery algorithm in accordance with the present disclosure may be utilized for treating at least one of atrial fibrillation and esophageal cancer or other cancers located around and near the heart without causing negative effects to a patient's heart during pulse delivery.

Figure 9:
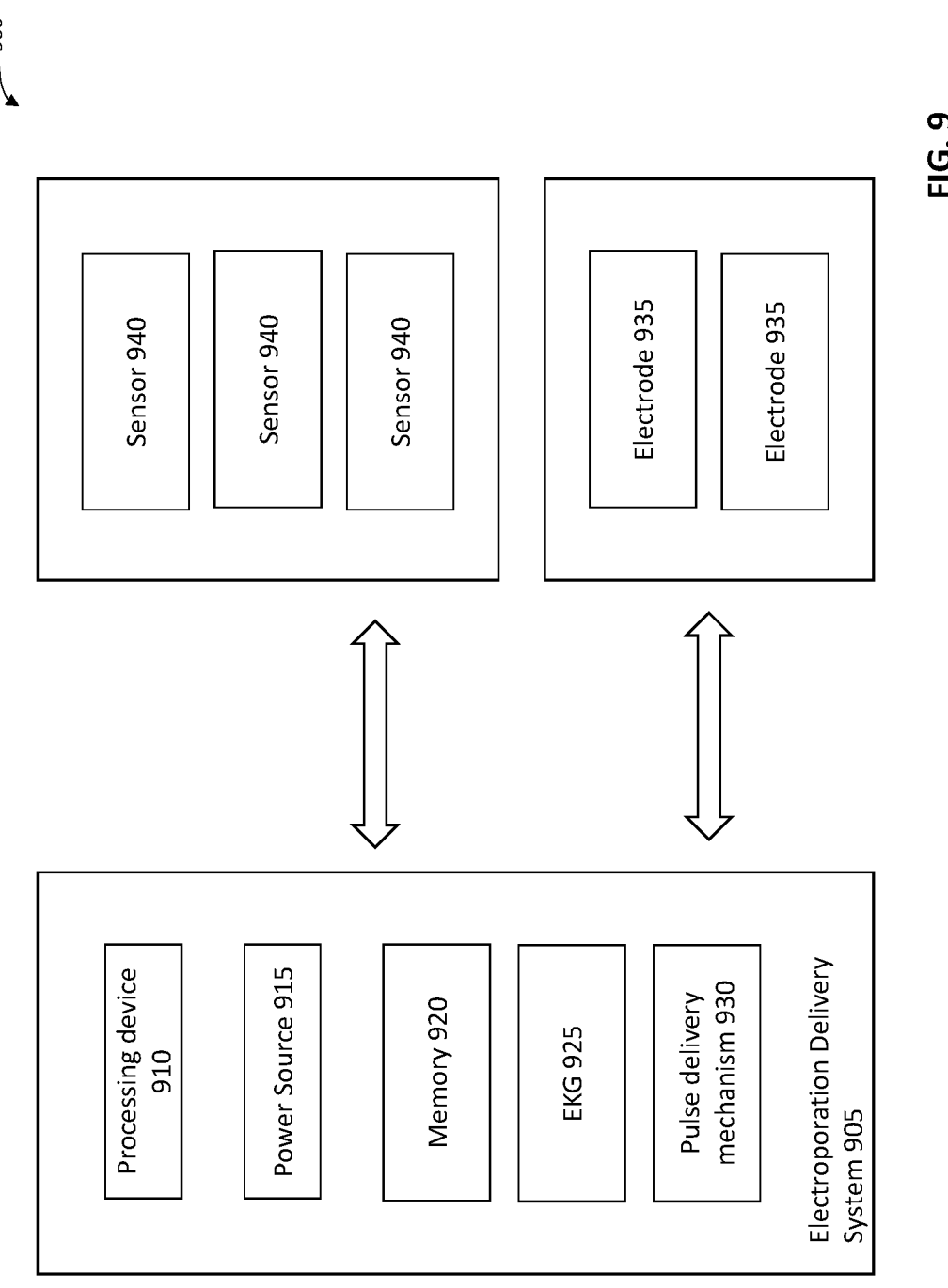
FIG. 9 illustrates an exemplary embodiment of an electroporation delivery system and components in accordance with the present disclosure.

An electroporation delivery system, such as an RE or IRE delivery system, of which an exemplary embodiment in accordance with the present disclosure is illustrated in the block diagram 900 of FIG. 9, may incorporate the algorithms described herein. In some embodiments, an electroporation delivery system 905 may include several components for operation, including but not limited to a processing device 910, a power source 915, a memory 920, an EKG/EGM 925, and a pulse delivery mechanism 930, which are described below. It is understood that at least a portion of the EKG/EGM 925 may be an internal and/or an external component of the electroporation delivery system 905. In some embodiments, the algorithms may be stored in the memory 920 for use by the processing device 910. The electroporation delivery system 905 may be operatively connected to one or more sensors 940, which may be attachable externally to a patient and/or insertable at selected internal locations of the patient, for measuring electrical activity of a patient's heart for the EKG/EGM 925. In some embodiments, the sensors 940 may be connected by wire connections, although the sensors 940 may be wirelessly connected. The electroporation delivery system 905 may also be operatively connected to one or more electrodes 935 for delivering pulses by the pulse delivery mechanism 930 in an electroporation treatment near the patient's heart. The electrodes may be configured for delivery to the heart and application of an electroporation pulse, with delivery platforms, e.g., an electroporation balloon catheter, for delivery of electroporation energy to treat tumors and other malignancies that would otherwise require electrocardiogram gaiting to avoid induction of arrhythmia. In some embodiments, individual electrodes may be placed in a retro-pericardial area around the heart.

In the following description, numerous specific details such as processor and system configurations are set forth in order to provide a more thorough understanding of the described embodiments. However, the described embodiments may be practiced without such specific details. Additionally, some well-known structures, circuits, and the like have not been shown in detail, to avoid unnecessarily obscuring the described embodiments.

One or more flow charts for carrying out the executed steps/methods of the disclosure may be provided. Although such figures presented herein may include a particular process flow, it can be appreciated that the flow charts merely provide an example of how the general functionality as described herein can be implemented. Further, the given flow charts do not necessarily have to be executed in the order presented unless otherwise indicated. In addition, the given processes may be implemented by a hardware element, a software element executed by a processor, or any combination thereof. For example, the processes may be implemented by a processor component executing instructions stored on an article of manufacture, such as a storage medium. A storage medium may comprise any non-transitory computer-readable medium or machine-readable medium, such as an optical, magnetic or semiconductor storage. The storage medium may store various types of computer executable instructions, such as instructions to implement one or more disclosed processes. Examples of a computer readable or machine readable storage medium may include any tangible media capable of storing electronic data, including volatile memory or non-volatile memory, removable or non-removable memory, erasable or non-erasable memory, writeable or re-writeable memory, and so forth. Examples of computer executable instructions may include any suitable type of code, such as source code, compiled code, interpreted code, executable code, static code, dynamic code, object-oriented code, visual code, and the like. The embodiments are not limited in this context.

Figure 2A:
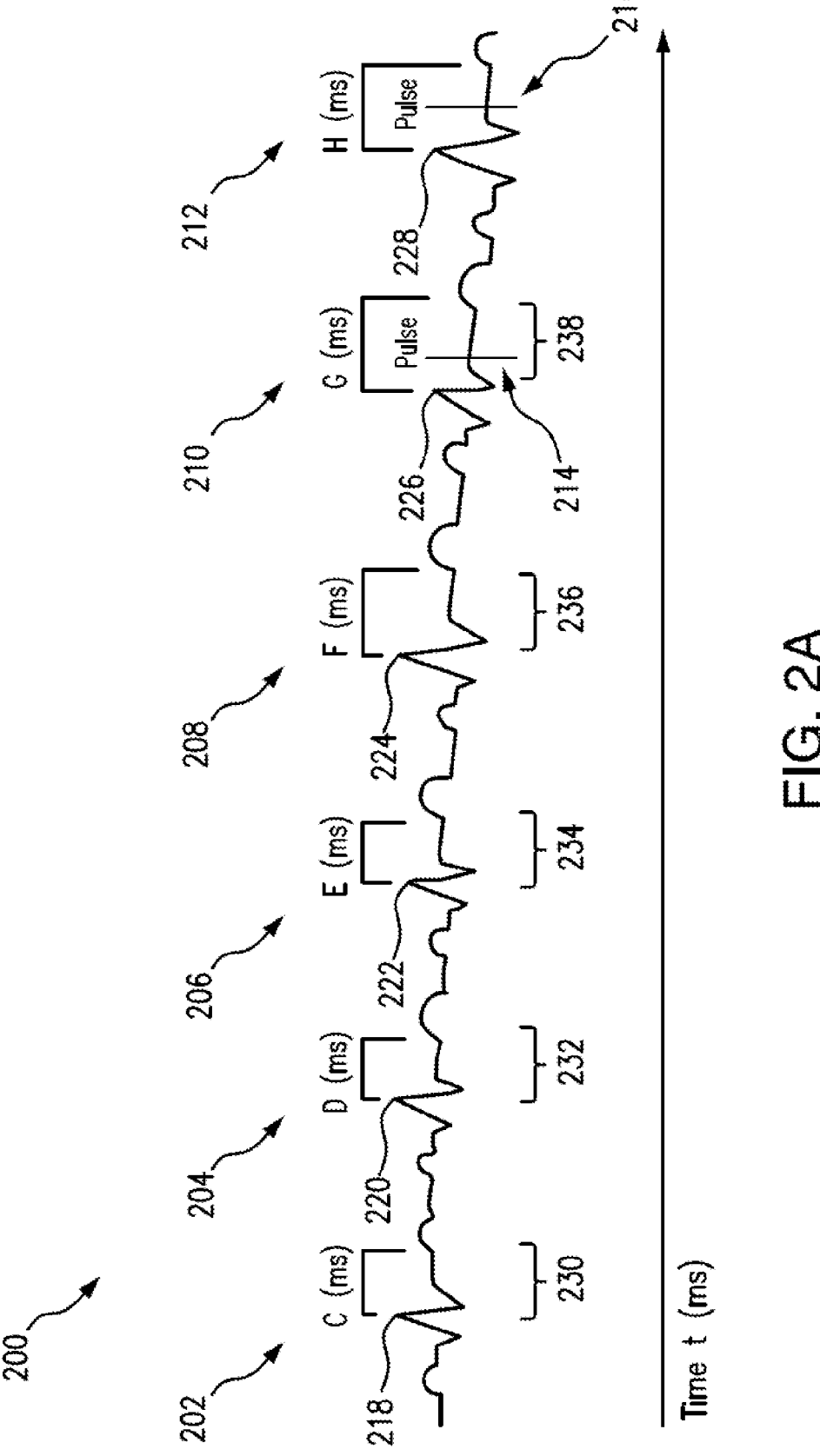
FIG. 2A illustrates an exemplary series of QRS complex wave monitoring in accordance with the present disclosure.
Figure 2B:
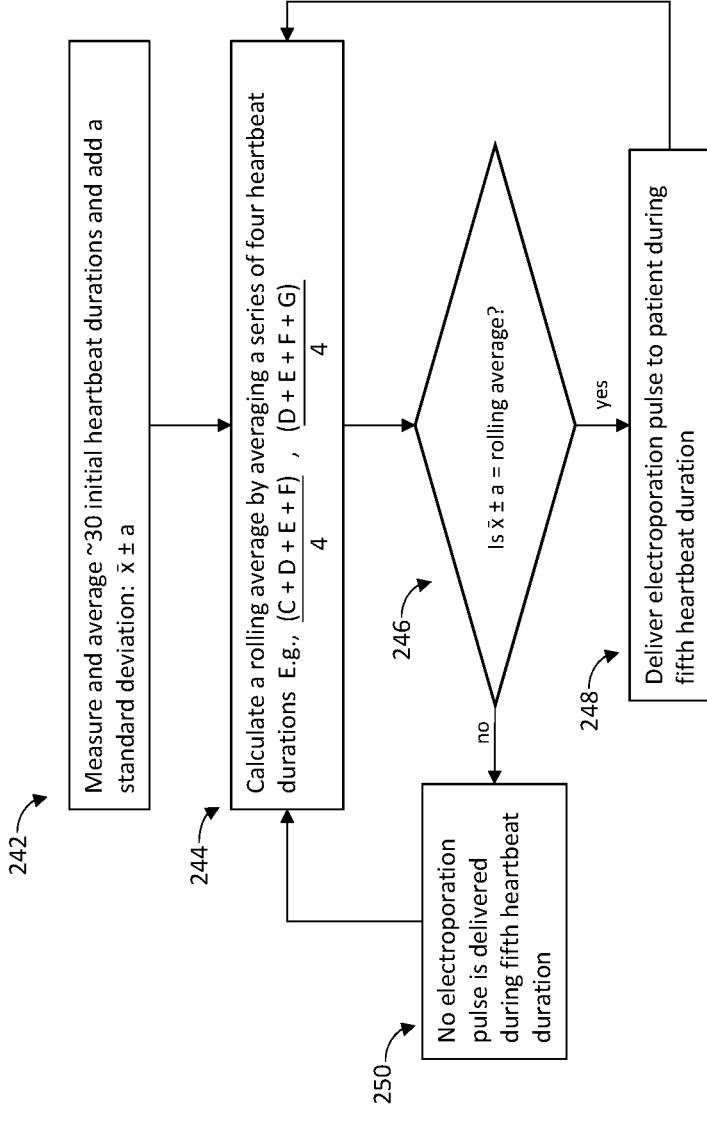
FIG. 2B illustrates a flow chart of an exemplary algorithm for electroporation pulse delivery based on FIG. 2A.

Referring now to FIG. 2A, a diagram of a series of QRS complex waves 200 of a patient's heartbeat over time are illustrated, and FIG. 2B, illustrating a flow chart 240 of an algorithm for use with an electroporation delivery system 905 (e.g., FIG. 9) of an exemplary embodiment in accordance with the present disclosure. The algorithms described herein may provide methods for operating an electroporation delivery system to deliver an electroporation pulse based on a patient's EKG/EGM. An algorithm used in an electroporation delivery system in accordance with an exemplary embodiment of the present disclosure may obtain a determined value, for example, by calculating an average $\bar{x}$ for approximately 30 initial pulse durations (ms), e.g., heartbeat durations, within a standard deviation a, at step 242. In some embodiments, a 95% confidence interval may be used, or $(1.96 \times standard\ deviation)/\sqrt{4}$, or 0.98*stdev. Although approximately 30 heartbeat durations may be measured, which may be measured in approximately 30 seconds, an average $\bar{x}$ may optionally be taken for approximately 10 to 45 heartbeat durations, so that a medical professional may still measure an average in under a minute before starting therapy. In other embodiments, the medical professional may optionally review the measured heartbeat durations, and approve the total number, or take additional measurements, before calculating the average.

$$average \sim 30\ heartbeat\ durations = \bar{x} \pm a \qquad (1)$$

A rolling average may be calculated by averaging a series of four pulse parameters, for example, a series of four heartbeat durations may be calculated to determine if an electroporation pulse should be delivered during the following heartbeat duration. The four heartbeat durations may be measured independently of the pulses used for determining the average heartbeat durations, although in other embodiments the four heartbeat durations may be included in the initial 30 heartbeat durations used to determine the average heartbeat duration. In some embodiments, the series may be greater or fewer than four heartbeat durations, although using fewer may be unusable if one is an irregular heartbeat. For example, heartbeat durations indicated at 202 area "C", 204 area "D", 206 area "E", 208 area "F", 210 area "G", and 212 area "H" illustrate exemplary heartbeat durations that may be used in calculating a rolling average, in milliseconds (ms). For example, heartbeat durations C, D, E, and F may be averaged to a first rolling average at step 244:

$$\frac{(C + D + E + F)}{4} \qquad (2)$$

Step 246 may compare the determined value to the rolling average, to determine that if a first rolling average of eq. (2) is equal to the average initial 30 heartbeat durations within a standard deviation a in eq. (1), then an electroporation pulse may be delivered in the fifth heartbeat duration following the averaged four heartbeat durations (e.g., C, D, E, F) during the absolute refractory period, e.g., heartbeat duration 210 area "G", as indicated at reference numeral 216 at step 248. In some embodiments, software may delay delivery and deliver a pulse in heartbeat duration 212 area "H", skipping the heartbeat duration 210 area "G", although it may be more advantageous to deliver the electroporation pulse during the heartbeat duration 210 area "G".

$$\text{if } \frac{(C + D + E + F)}{4} = \overline{x} \pm a, \qquad (3)$$

then pulse is delivered during G

However, if the first rolling average in eq. (2) is not equal to the average initial 30 heartbeat durations within a standard deviation a in eq. (1), then an electroporation pulse is not delivered in the fifth heartbeat duration following the average four heartbeat durations (e.g., C, D, E, F) during the absolute refractory period at step 250. Thus, the algorithm may consider an irregular heart rhythm and determine not to deliver the electroporation pulse during heartbeat duration 210 area "G".

$$\text{if } \frac{(C + D + E + F)}{4} \ne \overline{x} \pm a, \qquad (4)$$

then pulse is not delivered during G

The flow chart 240 illustrates that the process may continue by calculating another rolling average at step 244. For example, a second rolling average may next be calculated averaging heartbeat durations D, E, F, and G:

$$\frac{(D + E + F + G)}{4} \qquad (5)$$

The second rolling average of eq. (5) may then be compared to eq. (1), so that if the second rolling average is equal to the average initial 30 heartbeat durations within a standard deviation a at step 246, then an electroporation pulse may be delivered in the fifth heartbeat duration following the averaged four heartbeat durations (e.g., D, E, F, G) during the absolute refractory period, e.g., heartbeat duration 212 area "H", as indicated at reference numeral 216 at step 248.

$$\text{if } \frac{(D + E + F + G)}{4} = \overline{x} \pm a, \qquad (6)$$

then pulse is delivered during H

However, if the second rolling average in eq. (5) is not equal to the average initial 30 heartbeat durations within a standard deviation a in eq. (1), then an electroporation pulse is not delivered in the fifth heartbeat duration following the average four heartbeat durations (e.g., D, E, F, G) during the absolute refractory period at step 250. This may allow for large variances in the absolute refractory period as mentioned above. Thus, the algorithm may consider an irregular heart rate and determine not to deliver the electroporation pulse during heartbeat duration 212 area "H".

$$\text{if } \frac{(D + E + F + G)}{4} \ne \overline{x} \pm a, \qquad (7)$$

then pulse is not delivered during H

Subsequent rolling averages may be calculated via steps 244, 246, 248 and/or 250 until all electroporation pulses have been delivered. In some embodiments, the electroporation delivery system may determine that after a predetermined number of skipped heartbeat durations (e.g., the rolling average is not equal to the initial heartbeat durations within the standard deviation), the procedure is stopped, and/or an alarm may be generated.

Figure 3A:
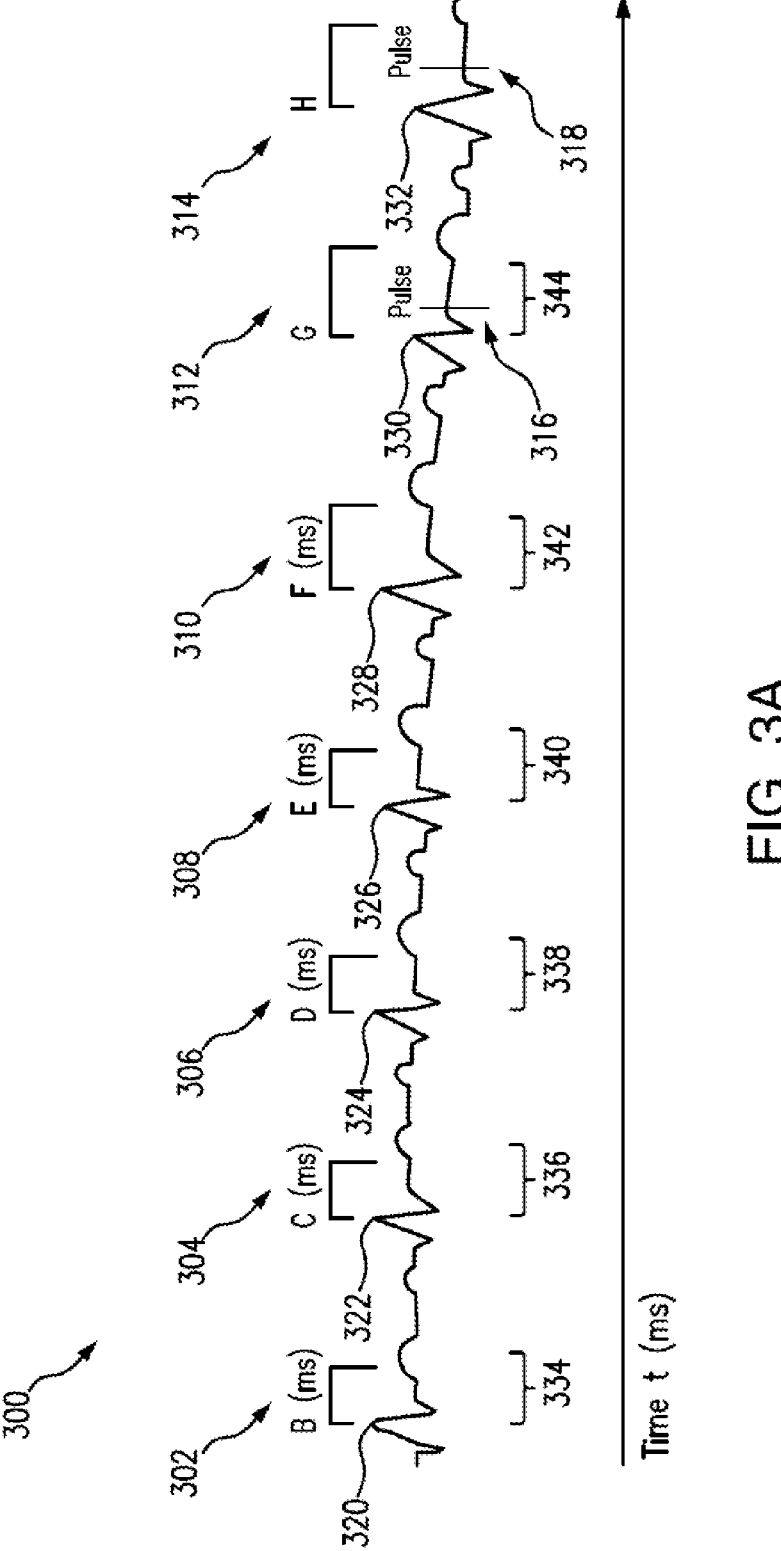
FIG. 3A illustrates another exemplary series of QRS complex wave monitoring in accordance with the present disclosure.
Figure 3B:
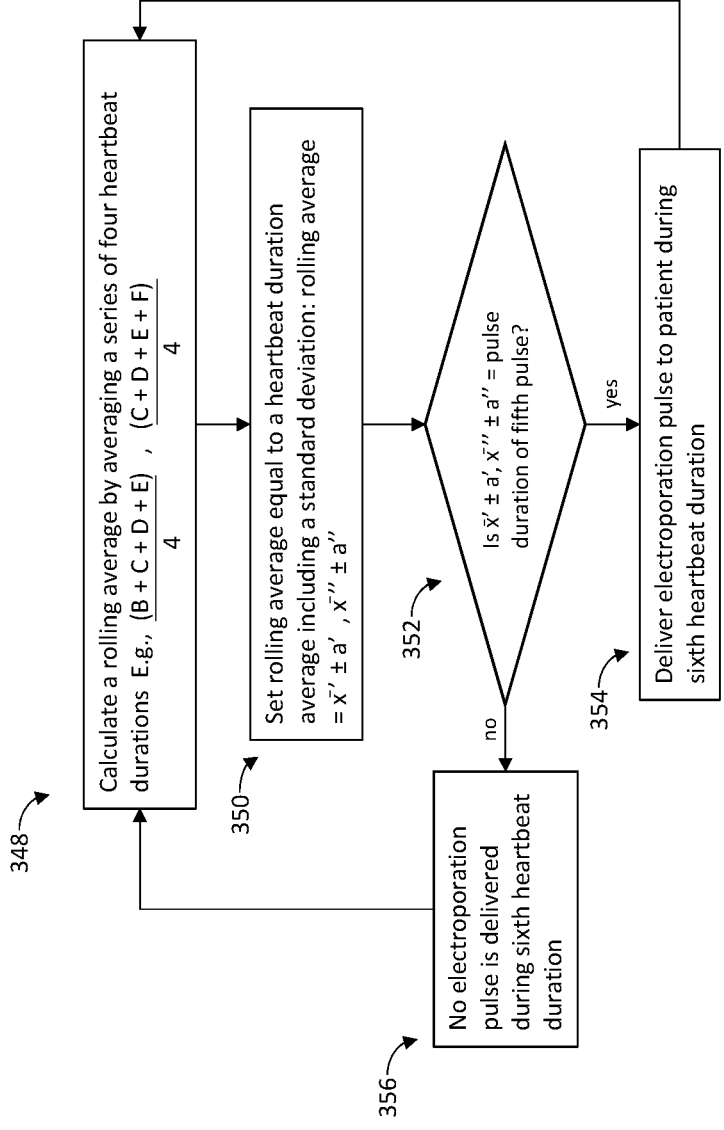
FIG. 3B illustrates a flow chart of an exemplary algorithm for electroporation pulse delivery based on FIG. 3A.

Referring now to FIG. 3A, a diagram of a series of QRS complex waves 300 over time are illustrated, and to FIG. 3B, illustrating a flow chart 346 of an algorithm for use with an electroporation delivery system 905 (e.g., FIG. 9) of an exemplary embodiment in accordance with the present disclosure. As described above with respect to FIGS. 2A-2B, an algorithm used in an electroporation delivery system in accordance with an exemplary embodiment of the present disclosure may calculate a rolling average by averaging a series of four heartbeat duration parameters, (e.g., pulse) including, for example, 302 area "B", 304 area "C", 306 area "C", 308 area "D", 310 area "E", 312 area "F", 314 area "G", and/or 316 area "H", which illustrate exemplary heartbeat durations in milliseconds (ms). In a first rolling average, heartbeat durations B, C, D, and E may first be averaged at step 348:

$$\frac{(B + C + D + E)}{4} \qquad (8)$$

This first rolling average calculated in eq. (8) may be set as a heartbeat duration average and within a standard deviation a', $\overline{x}' \pm a'$ at step 350. In some embodiments a 95% confidence interval may be used, or (1.96×standard deviation)/$\sqrt{4}$, or 0.98*stdev. The first rolling average is then compared to the determined value at step 352. In some embodiments, the determined value may be the following heartbeat duration, e.g., the fifth heartbeat duration "F". If the F heartbeat duration is equal to the heartbeat duration average within the standard deviation (e.g., ±0.98*stdev), then an electroporation pulse may be delivered during the subsequent sixth heartbeat duration "G" at step 354. In some embodiments, a combination of the amplitude and the rolling average may be used to determine a correct wave peak is being measured and whether the duration changes. In some embodiments, the electroporation pulse may be delivered at $\overline{x}/2$ ms after the Q wave of the G heartbeat duration indicated at reference numeral 312, where $\overline{x}$ is the four heartbeat duration rolling average that will adjust as the rolling averages continue. The rolling heartbeat duration average may help to maintain and validate the triggering reference point on the QRS wave complex so that the pulse may be reliably delivered between the S and T waves.

It may be assumed in some embodiments that the heartbeat duration is consistent enough for short periods of time and is not erratic so that if the rate of the heartbeat increases or decreases slowly, the electroporation pulsing will not stop automatically because the heartbeat may still be within normal range even if the pace changes. The electroporation delivery system may recognize that the pace changes, and adjust the algorithms to pulse in the correct place. If the heartbeat becomes irregular, e.g., an arrhythmia, the electroporation pulse delivery system may recognize it immediately since the pulses will not be within the rolling average range, so that the electroporation delivery system may alert a medical professional. In some embodiments, a' may be set as a constant in lieu of 0.98*stdev, which may provide a more consistent, and thereby safer, range.

$$\text{if } \frac{(B + C + D + E)}{4} = \bar{x}' \pm a' = F, \tag{9}$$

then pulse is delivered during G

However, if the F heartbeat duration is not equal to the rolling average within the standard deviation, then a pulse is not delivered during the G heartbeat at step 356. Thus, the algorithm may consider an irregular heart rhythm and determine not to deliver the electroporation pulse during 312 area "G".

$$\text{if } \frac{(B + C + D + E)}{4} = \bar{x}' \pm a' \neq F, \tag{10}$$

then pulse is not delivered during G

The flow chart 346 illustrates that the process may continue by calculating another rolling average at step 348. A second rolling average may be calculated, using heartbeat durations C, D, E, and F, which may be set as the average $\bar{x}''$ including a standard deviation a":

$$\frac{(C + D + E + F)}{4} = \bar{x}'' \pm a'' \tag{11}$$

The average calculated in eq. (11) may then be compared to subsequent fifth heartbeat duration G at step 352. If G is equal to the average within the standard deviation (e.g., a 95% confidence interval may be used, or (1.96×standard deviation)/√4, or 0.98*stdev), then an electroporation pulse may be delivered during heartbeat duration H, indicated at reference numeral 314 at step 354. In some embodiments, the electroporation pulse may be delivered at $\bar{x}/2$ ms after the Q wave of the heartbeat duration H.

$$\text{if } \frac{(C + D + E + F)}{4} = \bar{x}'' \pm a'' = G, \tag{12}$$

then pulse is delivered during H

However, if the heartbeat duration G is not equal to the rolling average within the standard deviation, then an electroporation pulse is not delivered during the heartbeat duration H at step 356. This may allow for large variances in the absolute refractory period as mentioned above.

$$\text{if } \frac{(C + D + E + F)}{4} = \bar{x}'' \pm a'' \neq G, \tag{13}$$

then pulse is not delivered during H

Subsequent rolling averages may be calculated via steps 348, 350, 352, 354, and/or 356 until all electroporation pulses have been delivered. In some embodiments, the electroporation delivery system may determine that after a predetermined number of skipped pulses (e.g., the rolling average within the standard deviation is not equal to the subsequent fifth heartbeat duration), the procedure is stopped, and/or an alarm may be generated. For example, if more than two electroporation pulses fail to be delivered (e.g., based on equations 10,13), a warning may be sent to an operator of the electroporation delivery system, so that the operator may determine whether to continue the procedure. The electroporation delivery system may further be configured to automatically shut-down operation after a predetermined number of missed heartbeats (e.g., four) if an operator fails to respond. This may be advantageous to help ensure patient safety when an irregular heart rate is determined.

Figure 2C:
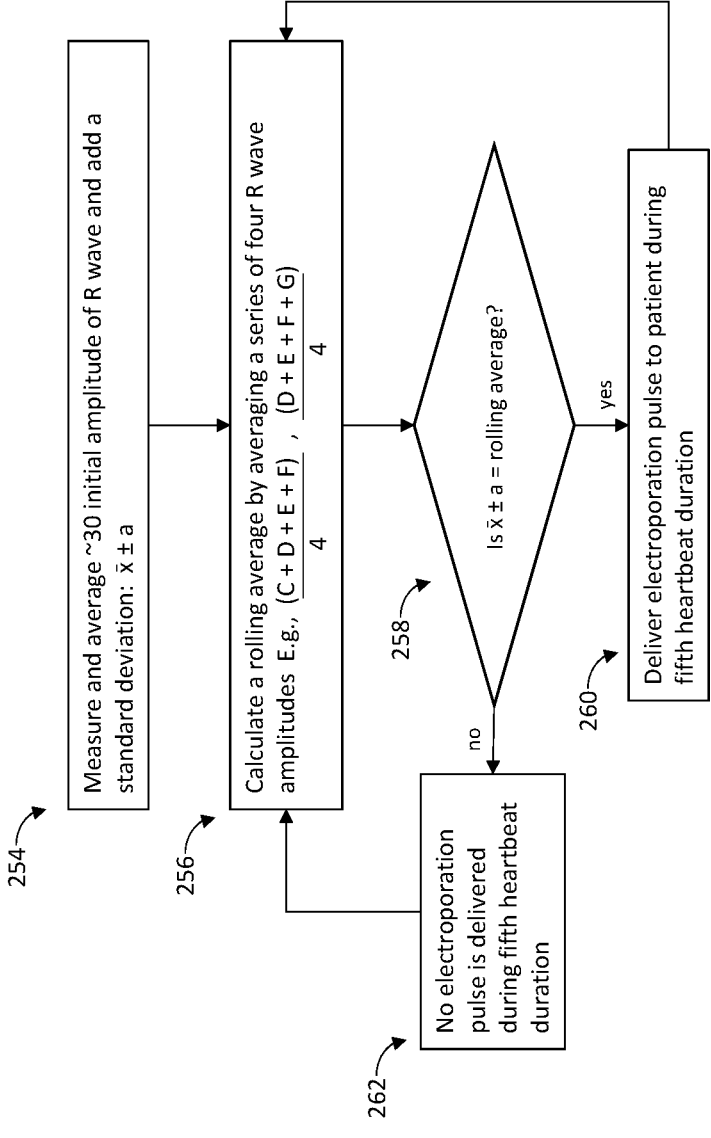
FIG. 2C illustrates a flow chart of another exemplary algorithm for electroporation pulse delivery based on FIG. 2A.
Figure 3C:
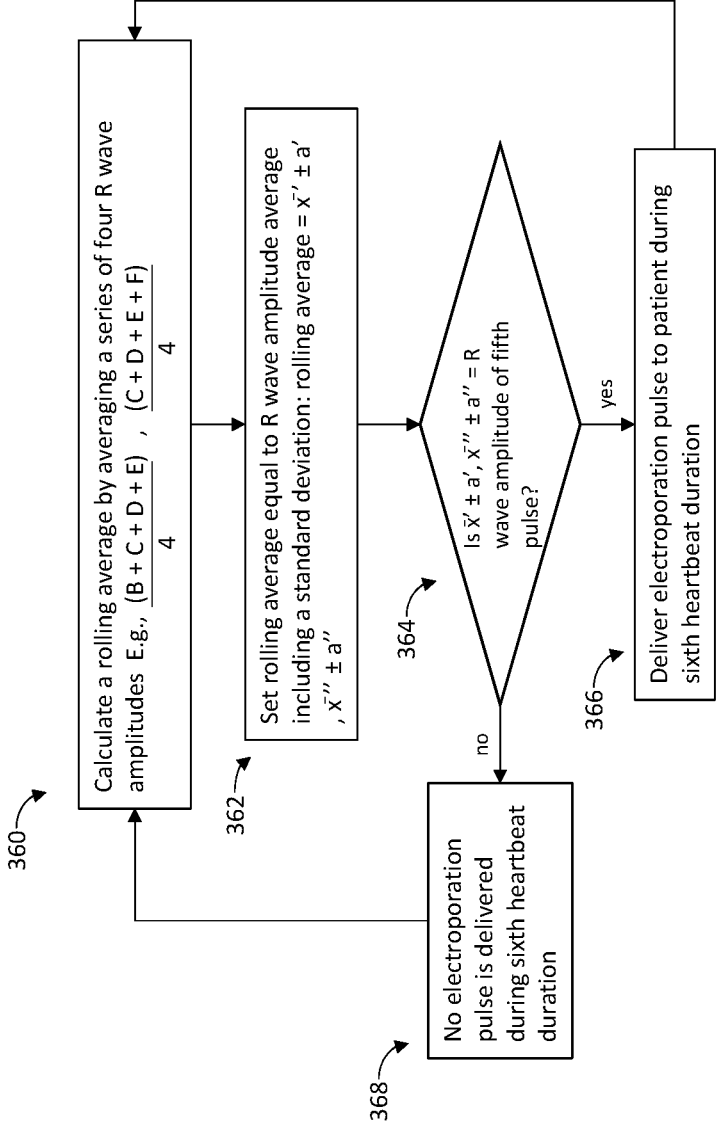
FIG. 3C illustrates a flow chart of an exemplary algorithm for electroporation pulse delivery based on FIG. 3A.

Another exemplary embodiment of an algorithm in accordance with the present disclosure, and illustrated by flow chart 252 of FIG. 2C and flow chart 358 of FIG. 3C may include utilizing an amplitude of the R wave as the heartbeat parameter. For example, indicated at reference numerals 218, 220, 222, 224, 226, and 228, an average amplitude may be calculated as a rolling average similar to equations (2), (5), and (8). At step 256 a first rolling average may be taken by averaging a series of the amplitudes of the R wave indicated at reference numerals 218 of duration C, 220 of duration D, 222 of duration E, and 224 of duration F. If the rolling average is equal to the determined value at step 258, the electroporation pulse may be delivered during the subsequent fifth heartbeat duration G (see FIGS. 2A-2C) at step 260. In some embodiments, the determined value may be an average of 30 initial amplitudes of R waves within a standard deviation (e.g., $\bar{x} \pm a$, where a is the 95% confidence interval described above) calculated at step 254. If the compared determined value and the averaged series of the pulse parameter (e.g., R wave amplitude) are not equal, then at step 262 no electroporation pulse is delivered. Subsequent rolling averages may be calculated via steps 256, 258, 260, and/or 262 until all electroporation pulses have been delivered.

Averages may also be calculated as described similar to FIGS. 3A-3B, in that at step 360 first rolling average may be taken by averaging a series of heartbeat parameters (e.g., amplitudes of the R wave) indicated at reference numerals 320 of heartbeat duration B, 322 of heartbeat duration C, 324 of heartbeat duration D, and 326 of heartbeat duration E, and setting it equal to the average amplitude within a standard deviation at step 362. If the average is equal to a determined value (e.g., an amplitude 328 of heartbeat duration F) at comparison step 364, then an electroporation pulse may be delivered during heartbeat duration G indicated by reference numeral 312 (see FIGS. 3A-3C) at step 366, and if they are not equal, then at step 368 no electroporation pulse is delivered. In some embodiments, the electroporation pulse may be deliverable by an electroporation delivery system within 50 ms. Subsequent rolling averages may be calculated via steps 360, 362, 364, 366, and/or 368 until all electroporation pulses have been delivered.

If a pulse will be delivered after 50 ms, some embodiments may utilize an average distance from the S wave to the T wave to determine if a delivered pulse is safe 50 ms after the R wave. The distance from the S wave to the T wave, for example, is indicated at reference numerals 230, 232, 234, 236, and 238 of FIG. 2A, or 334, 336, 338, 340, 342, and 344 of FIG. 3A. If the averaged distance between the S and T waves is greater than 50 ms plus two electroporation pulse durations (ms), and the amplitude for the R wave is satisfied, then an electroporation pulse may be delivered. Two pulse durations may be used as a standard offset measurement to ensure one pulse may be delivered safely even if the refractory period is slightly faster. Using one heartbeat duration may allow a pulse delivery on the T wave if the refractory period increases, thereby potentially causing an arrhythmia. More than two electroporation pulse durations may be excessive in the event of long pulse widths. In some embodiments, instead of a constant two pulse durations, the offset may be the total time of pulse delivery per trigger multiplied by a constant, e.g., 1.25, or 1.5.

Figure 4:
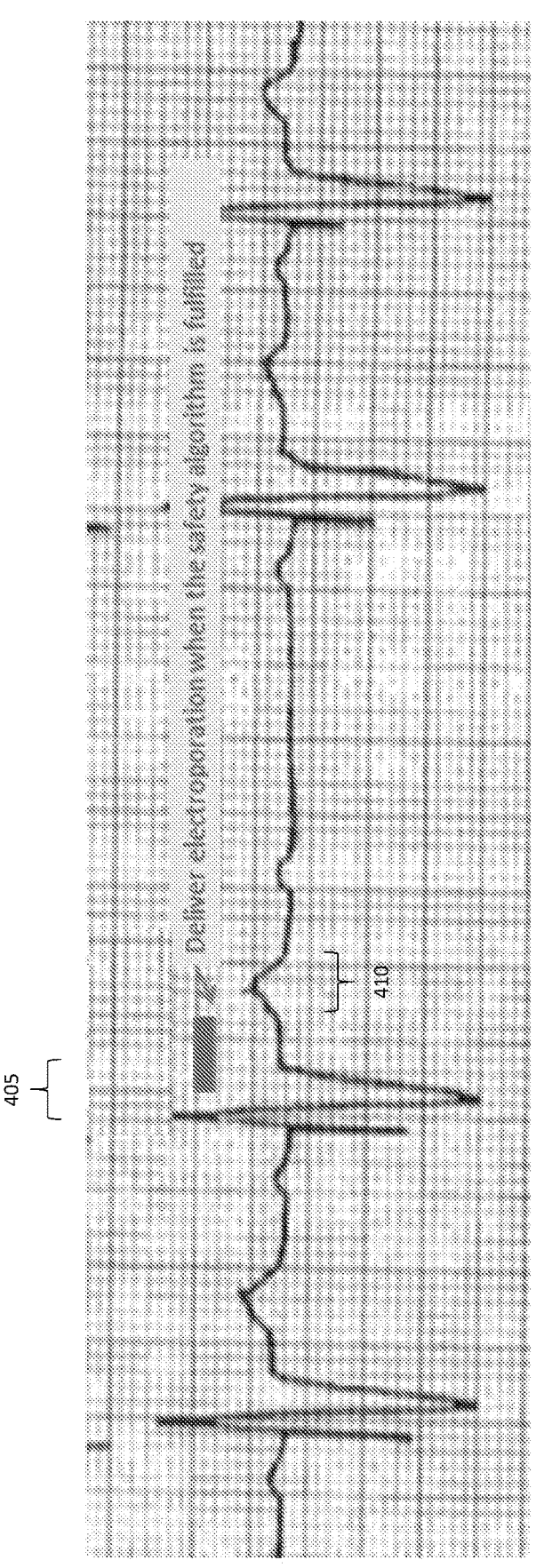
FIG. 4 illustrates another exemplary series of QRS complex wave monitoring using filters in accordance with the present disclosure.

An exemplary embodiment of an algorithm in accordance with the present disclosure may include an "And Statement" using filters for monitoring the QRS wave, or the EKG/EGM, or in some embodiments, the EGM wave, if a CS catheter is used for internal measurements. The wave signal may be split before entering a first filter A, or a second filter B. The filters A, B may reduce background noise to enhance the selected wave portions. For example, filter A may only detect the R wave, and filter B may only detect the T wave due to their different frequencies. When detecting noise it may be positive and while not detecting noise it may negative. The filters A, B may be advantageous when an EKG/EGM is less distinguishable between the T and R waves. In some embodiments, the A filter may extract the R wave (in a QRS wave), or G wave (in an EGM wave), and the B filter may extract the T wave. As shown in FIG. 4, an exemplary embodiment of a series of EKG/EGM wave signals 400 includes an R wave indicated at reference numeral 405 and a T wave indicated at reference numeral 410.

If the output of the A filter is positive, and the output of the B filter is negative, then an electroporation pulse may be delivered. However, if the output of the A filter is positive, and the output of the B filter is also positive, then the electroporation delivery system will not deliver a pulse. Both A and B may be negative during the refractory period for a pulse to be delivered. The pulse may be delivered approximately 50 ms after the R wave is detected, if the output of the B filter is negative, to be safe for most heart rhythms. In some embodiments, a pulse may safely be delivered up to approximately 70 ms after the R wave is detected, where the refractory period is approximately 250 ms. In some embodiments, instead of a constant 70 ms, a pulse may be safely delivered by: an average refractory period of the patient—1.25*pulse length, or 1.25*total number of pulses delivered per trigger event. In some embodiments, as an additional safety feature, detecting the T wave may ensure the refractory period isn't changing so that in the event the T wave (+) is detected, the delivery system is stopped. In some embodiments, an electroporation pulse may be deliverable between the R wave and T wave by detecting a T wave's absence, e.g., filter B does not detect any wave presence. If a T wave is detected at any point during pulsing, the delivery system may immediately stop pulsing.

Figure 1A:
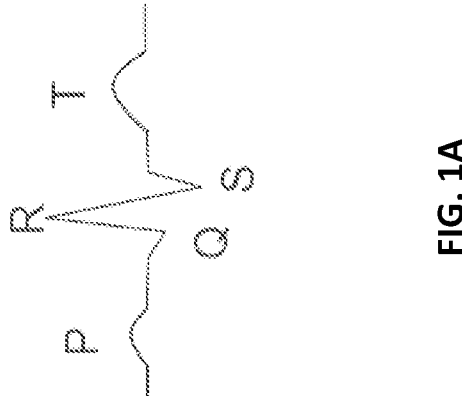
FIG. 1A illustrates a QRS complex wave of a healthy heart.

Some embodiments may induce pacing, for example, before electroporation pulse delivery, during electroporation pulse delivery, and/or after electroporation pulse delivery. Pacing may also be utilized for a patient having a regular heartbeat (e.g., a heartbeat having a QRS wave complex as illustrated in FIG. 1A) or irregular heartbeat (e.g., a heartbeat having a QRS wave complex as illustrated in FIG. 1B), and may be applied to a portion of the patient's heart, e.g., a ventricular portion. It may be advantageous to use pacing for patients having any of a fast, regular, or irregular heartbeat so that the refractory period may be controllable and it may be known exactly when to deliver a pulse. The heart rhythm may be monitored, e.g., by monitoring the electrocardiogram (EKG, EGM), for a regular and/or irregular heartbeat and heart rate. Pacing may be advantageous because long pace intervals will increase the refractory period, to safely deliver one to a plurality of electroporation pulses per heartbeat, thereby delivering therapy faster. In some embodiments, electroporation pulse delivery may be between 1 and 100 between heartbeats. In some embodiments, a pacing signal may be delivered so that a patient's heartbeat is adjusted, e.g., slowed, and after a predetermined amount of time from delivery of the pacing signal, an electroporation pulse may be delivered. Pacing may be accomplished via the right side ventricle of a patient's heart, although a pharmaceutical drug dosage may be used in addition to or instead of to adjust, e.g., slow, the heart pace. In some embodiments, pacing simulating a heartbeat may be applied continuously throughout a procedure.

Figure 5:
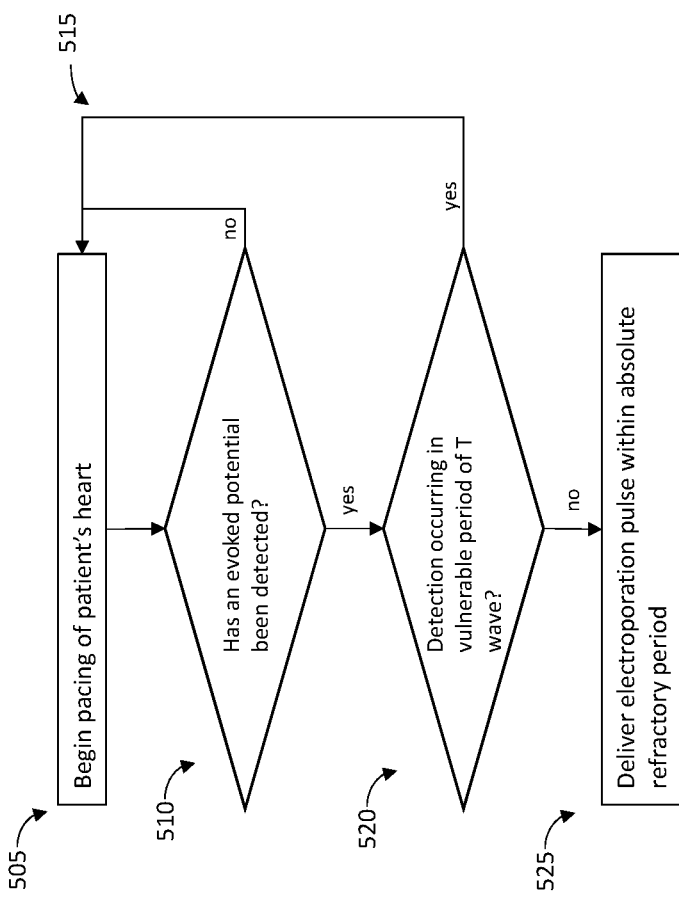
FIG. 5 illustrates a flow chart of an exemplary embodiment of a method for pacing a patient's heart for electroporation pulse delivery in accordance with the present disclosure.

FIG. 5 illustrates a flow chart 500 of an exemplary process for pacing and delivery of an electroporation pulse. At step 505, a pacing signal is applied to a patient's heart to slow the heart rate. In some embodiments, the pacing signal may be applied continuously. At step 510, the electroporation delivery system may determine if an evoked potential, an electrical potential recorded from the patient's nervous system, is detected. If not, the electroporation delivery system does not deliver an electroporation pulse at 515, and is looped back to continue pacing the patient's heart at step 505. If an evoked potential has been detected, at step 520 the electroporation delivery system determines if the patient is in a vulnerable portion of the EKG/EGM wave signal, in particular, in the vulnerable period of the T wave. If yes, then the electroporation delivery system does not deliver an electroporation pulse at step 515 and is looped back to pacing the patient's heart at step 505. If the patient is not in a vulnerable period of the T wave, the electroporation delivery system may deliver an electroporation pulse within an absolute refractory period at step 525. A T wave is a period in the heart where different tissues repolarize at different rate, which, as a result, may create a repolarization gradient, and stimulation with direct current on cardiac tissue when such a gradient is present may promote (or nullify) the induction of highly malignant ventricular arrhythmias including a polymorphic ventricular tachycardia and ventricular fibrillation.

In some embodiments, induced pacing may occur only prior to electroporation pulse delivery, although other embodiments may include pacing a patient's heartbeat during and/or after electroporation pulse delivery as well. Slowing the pace of a patient's heart by induced pacing may be advantageous because it may elongate the refractory period, thereby preventing undesirable heart rhythm side effects. In some embodiments, pacing may be utilized with the "And Statement" as described above with respect to FIG. 4, which may be advantageous to provide more electroporation pulses, either in frequency, amount, or amplitude, to regulate heart rhythm by electroporating cardiac cells and stopping the circuit or triggering site for the patient's arrhythmia.

Figure 6:
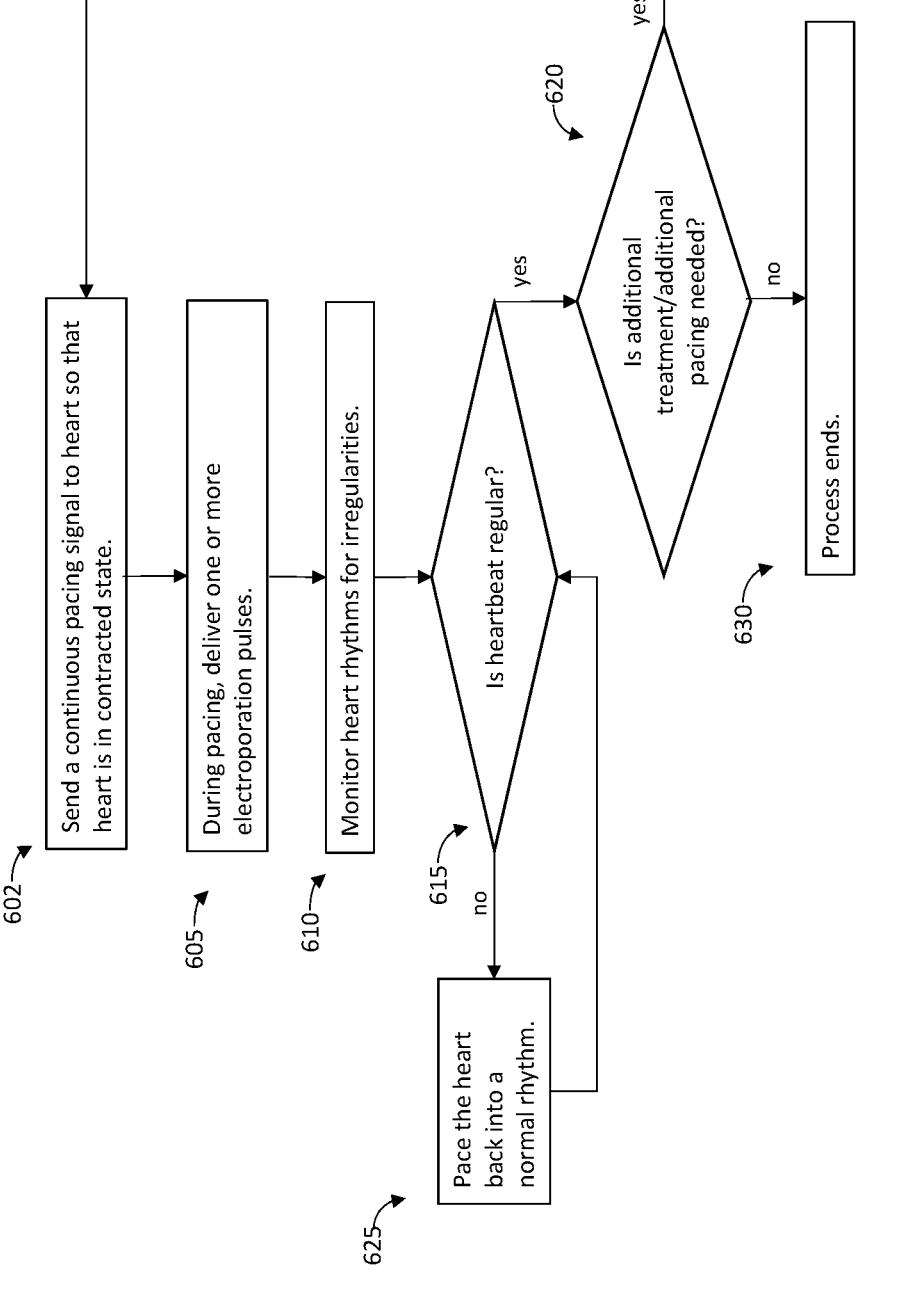
FIG. 6 illustrates another flow chart of an exemplary embodiment of a method for pacing a patient's heart for electroporation pulse delivery in accordance with the present disclosure.

In some embodiments, a patient's heart may be continuously paced by the electroporation delivery system, or an external pacing device. FIG. 6 illustrates a flow chart 600 of an exemplary process for continuous pacing and electroporation pulse delivery. It may be advantageous to monitor a heart rate continuously for the heart rate and any irregularities, e.g., every other heartbeat duration, or a time period of a couple seconds, so that the continuous pacing and electroporation pulse delivery process will be a continuous process of check and pulse. At 602, a continuous pacing signal may be directed to at least one of the right ventricle of the heart and the area of interest. Sending a continuous pacing signal may result in the heart being in a prolonged contracted state. In some instances, the contracted state may last approximately 1 to 15 seconds. While a patient's heart is in the contracted state by the continuous pacing signal being sent at step 605, the electroporation delivery system may deliver one or more electroporation pulses. It may be advantageous to contract the heart by a continuous pacing signal, as in a contracted state, the electroporation pulse may not cause irregular heartbeats. In embodiments, a pacing signal may be delivered to a patient's heart for at least one of a predetermined amount of time and a predetermined number of pulses. At step 610, the patient's heart may be monitored by pausing, or stopping pacing to determine if there are any arrhythmias or if the heartbeat is regular. Pacing may be paused or otherwise stopped so heart rhythms may be monitored for several heartbeats at step 615. In embodiments, the monitoring may occur over at least one of a predetermined amount of time and a predetermined number of heartbeats. If the heartbeat is regular, the system may determine at step 620 if additional pulses are needed. If the heartbeat is irregular, then the delivery system may pace the heart back into a normal rhythm at step 625. Steps 615 and 625 may repeat until the heart has a normal rhythm. If additional treatment is needed, e.g., more electroporation pulses should be delivered, pacing may be continued so that additional pulses may be delivered to complete treatment by returning to step 602. Once treatment is complete, at step 630 the process may end. Slowing the pace of a patient's heart by continuous pacing may be advantageous because it may keep it in a contracted state, thereby preventing the electroporation pulses from causing undesirable heart rhythm side effects.

In some embodiments, electroporation pulse delivery may be paused or stopped for monitoring a patient's heart EKG/EGM. This may be advantageous during a prolonged ablation treatment by the electroporation delivery system, so that an operator or medical professional may determine that the electroporation pulsing has not caused the patient's heart to go into an arrhythmia. Upon confirmation that the patient's heart rhythms are normal, the electroporation delivery system may continue operation as needed.

Figure 8:
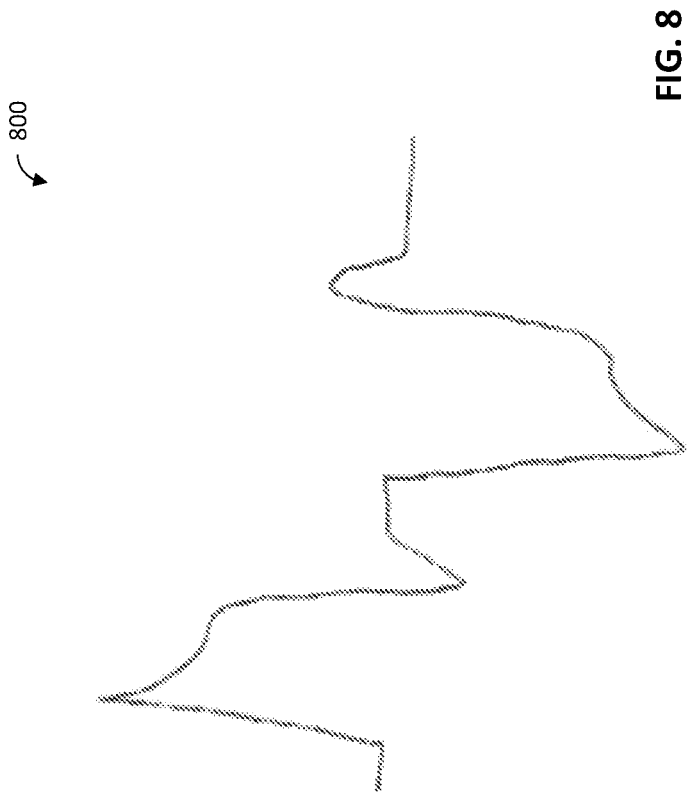
FIG. 8 illustrates another exemplary embodiment of a wave pulse shape in accordance with the present disclosure.
Figure 7:
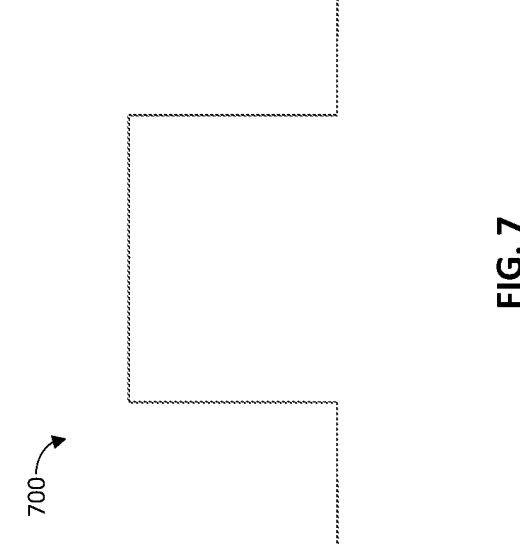
FIG. 7 illustrates an exemplary embodiment of a wave pulse shape in accordance with the present disclosure.

The electroporation pulse may be any of a variety of shapes, and may be determined by electronics of the electroporation delivery system and their ability to control the release of energy. In some embodiments, the electroporation delivery system may deliver a pulse having at least one of a square-shaped as shown in FIG. 7, and a defibrillation-like wave as shown FIG. 8. Additionally, the square-shaped wave and the defibrillation-like wave may be monopolar or bipolar. For example, FIG. 7 illustrates a square-shaped monopolar wave pulse 700, and FIG. 8 illustrates a defibrillation-like bipolar wave pulse 800. In embodiments, the square wave pulse shape may be positive, negative, and/or a combination of positive and negative. The shape of the electroporation pulse may affect a particular response in the patient's heart. Although "a pulse" may be described herein, it is understood that one or more square wave pulses may be delivered between each heartbeat.

Referring back to FIG. 9, the electroporation delivery system 905 may execute processing operations or logic for the monitoring of the patient and electroporation pulse delivery using the processing device 910. The processing device 910 may comprise various hardware elements, software elements, or a combination of both. Examples of hardware elements may include devices, logic devices, components, processors, microprocessors, circuits, processor circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

In some embodiments, the electroporation delivery system 905 may execute communications operations or determination of delivery an electroporation pulse using a communications component (not shown). The communications component may implement any well-known communications techniques and protocols, such as techniques suitable for use with packet-switched networks (e.g., public networks such as the Internet, private networks such as an enterprise intranet, and so forth), circuit-switched networks (e.g., the public switched telephone network), or a combination of packet-switched networks and circuit-switched networks (with suitable gateways and translators). The communications component may include various types of standard communication elements, such as one or more communications interfaces, network interfaces, network interface cards (NIC), radios, wireless transmitters/receivers (transceivers), wired and/or wireless communication media, physical connectors, and so forth. By way of example, and not limitation, communication media may include wired communications media and wireless communications media. Examples of wired communications media may include a wire, cable, metal leads, printed circuit boards (PCB), backplanes, switch fabrics, semiconductor material, twisted-pair wire, co-axial cable, fiber optics, a propagated signal, and so forth. Examples of wireless communications media may include acoustic, radio-frequency (RF) spectrum, infrared and other wireless media.

Figure 10:
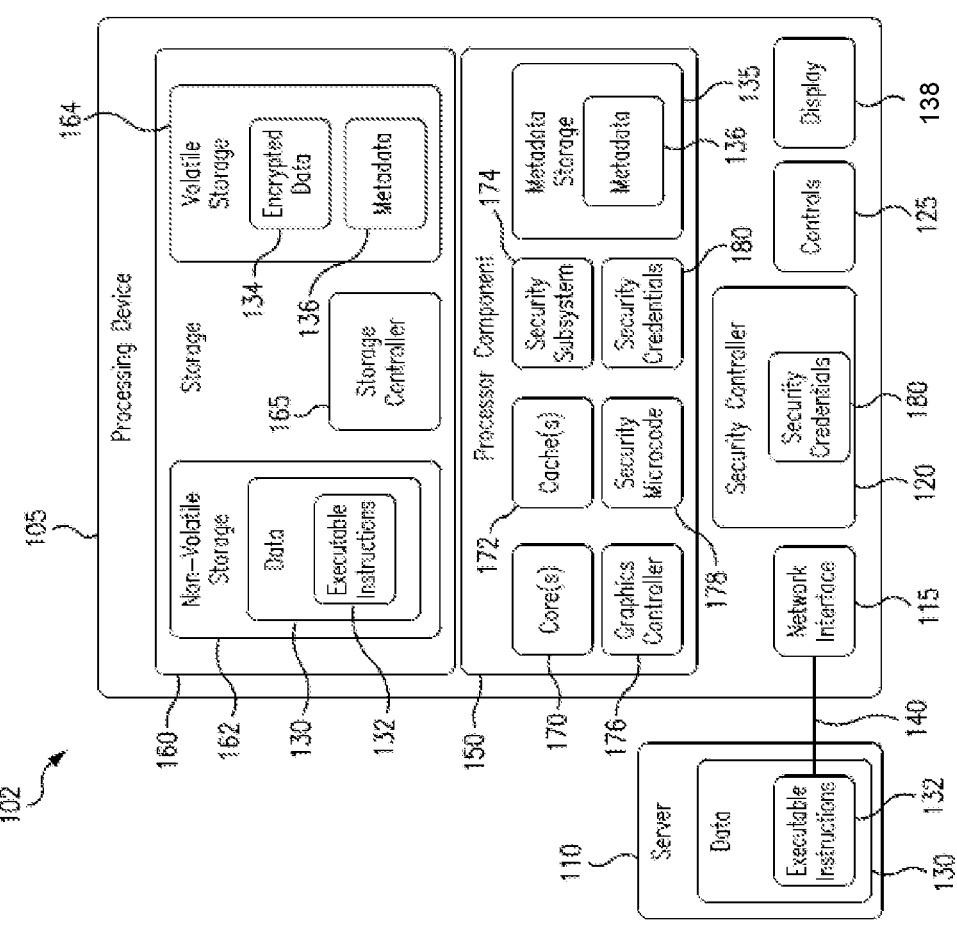
FIG. 10 illustrates an exemplary embodiment of a processing device of an electroporation delivery system in accordance with the present disclosure.

Turning now to FIG. 10, illustrated is an example of an operating environment, which may be used monitor and determine when to deliver electroporation pulses to a patient, a system 102 may include a server 110 and a processing device 105, which may be the same or similar to the electroporation delivery system 905 of FIG. 9, coupled via a network 140. Server 110 and processing device 105 may exchange data 130 via network 140, and data 130 may include executable instructions 132 for execution within processing device 105. In some embodiments, data 130 may be include data values, executable instructions, and/or a combination thereof. In other embodiments, data 130 may include sensor metric data from the sensors 940 and electrode data from the electrodes 935 of FIG. 9. Network 140 may be based on any of a variety (or combination) of communications technologies by which signals may be exchanged, including without limitation, wired technologies employing electrically and/or optically conductive cabling, and wireless technologies employing infrared, radio frequency, and/or other forms of wireless transmission.

In various embodiments, processing device 105 may incorporate a processor component 150, which may be the same or similar to the processing device 910 of FIG. 9, a storage 160, controls 125 (for instance, manually-operable controls), a display 138 and/or a network interface 115 to couple the processing device 105 to the network 140. Processor component 150 may incorporate security credentials 180, a security microcode 178, metadata storage 135 storing metadata 136, a security subsystem 174, one or more processor cores 170, one or more caches 172 and/or a graphics controller 176. Storage 160 may include volatile storage 164, non-volatile storage 162, and/or one or more storage controllers 165. Processing device 105 may include a controller 120 (for example, a security controller) that may include security credentials 180. Controller 120 may also include one or more of the embodiments described herein for unified hardware acceleration of hash functions.

Volatile storage 164 may include one or more storage devices that are volatile in as much as they require the continuous provision of electric power to retain information stored therein. Operation of the storage device(s) of volatile storage 164 may be controlled by storage controller 165, which may receive commands from processor component 150 and/or other components of processing device 105 to store and/or retrieve information therein, and may convert those commands between the bus protocols and/or timings by which they are received and other bus protocols and/or timings by which the storage device(s) of volatile storage 164 are coupled to the storage controller 165. By way of example, the one or more storage devices of volatile storage 164 may be made up of dynamic random access memory (DRAM) devices coupled to storage controller 165 via an interface, for instance, in which row and column addresses, along with byte enable signals, are employed to select storage locations, while the commands received by storage controller 165 may be conveyed thereto along one or more pairs of digital serial transmission lines.

Non-volatile storage 162 may be made up of one or more storage devices that are non-volatile inasmuch as they are able to retain information stored therein without the continuous provision of electric power. Operation of storage device(s) of non-volatile storage 162 may be controlled by storage controller 165 (for example, a different storage controller than used to operate volatile storage 164), which may receive commands from processor component 150 and/or other components of processing device 105 to store and/or retrieve information therein, and may convert those commands between the bus protocols and/or timings by which they are received and other bus protocols and/or timings by which the storage device(s) of non-volatile storage 162 are coupled to storage controller 165. By way of example, one or more storage devices of non-volatile storage 162 may be made up of ferromagnetic disk-based drives (hard drives) operably coupled to storage controller 165 via a digital serial interface, for instance, in which portions of the storage space within each such storage device are addressed by reference to tracks and sectors. In contrast, commands received by storage controller 165 may be conveyed thereto along one or more pairs of digital serial transmission lines conveying read and write commands in which those same portions of the storage space within each such storage device are addressed in an entirely different manner.

Processor component 150 may include at least one processor core 170 to execute instructions of an executable routine in at least one thread of execution. However, processor component 150 may incorporate more than one of processor cores 170 and/or may employ other processing architecture techniques to support multiple threads of execution by which the instructions of more than one executable routine may be executed in parallel. Cache(s) 172 may include a multilayer set of caches that may include separate first level (L1) caches for each processor core 170 and/or a larger second level (L2) cache for multiple ones of processor cores 170.

In some embodiments in which processing device 105 includes display 138 and/or graphics controller 176, one or more cores 170 may, as a result of executing the executable instructions of one or more routines, operate controls 125 and/or the display 138 to provide a user interface and/or to perform other graphics-related functions. Graphics controller 176 may include a graphics processor core (for instance, a graphics processing unit (GPU)) and/or component (not shown) to perform graphics-related operations, including and not limited to, decompressing and presenting a motion video, rendering a 2D image of one or more objects of a three-dimensional (3D) model, etc.

Non-volatile storage 162 may store data 130, including executable instructions 132. In the aforementioned exchanges of data 130 between processing device 105 and server 110, processing device 105 may maintain a copy of data 130, for instance, for longer term storage within non-volatile storage 162. Volatile storage 164 may store encrypted data 134 and/or metadata 136. Encrypted data 134 may be made up of at least a portion of data 130 stored within volatile storage 164 in encrypted and/or compressed form according to some embodiments described herein. Executable instructions 132 may make up one or more executable routines such as an operating system (OS), device drivers and/or one or more application routines to be executed by one or more processor cores 170 of processor component 150. Other portions of data 130 may include data values that are employed by one or more processor cores 170 as inputs to performing various tasks that one or more processor cores 170 are caused to perform by execution of executable instructions 132.

As part of performing the executable instructions 132, one or more processor cores 170 may retrieve portions of executable instructions 132 and store those portions within volatile storage 164 in a more readily executable form in which addresses are derived, indirect references are resolved and/or links are more fully defined among those portions in the process often referred to as loading. As familiar to those skilled in the art, such loading may occur under the control of a loading routine and/or a page management routine of an OS that may be among executable instructions 132. As portions of data 130 (including portions of executable instructions 132) are so exchanged between non-volatile storage 162 and volatile storage 164, security subsystem 174 may convert those portions of data 130 between what may be their original uncompressed and unencrypted form as stored within non-volatile storage 162, and a form that is at least encrypted and that may be stored within volatile storage 164 as encrypted data 134 accompanied by metadata 136.

Security subsystem 174 may include hardware logic configured or otherwise controlled by security microcode 178 to implement the logic to perform such conversions during normal operation of processing device 105. Security microcode 178 may include indications of connections to be made between logic circuits within the security subsystem 174 to form such logic. Alternatively or additionally, security microcode 178 may include executable instructions that form such logic when so executed. Either security subsystem 174 may execute such instructions of the security microcode 178, or security subsystem 174 may be controlled by at least one processor core 170 that executes such instructions. Security subsystem 174 and/or at least one processor core 170 may be provided with access to security microcode 178 during initialization of the processing device 105, including initialization of the processor component 150. Further, security subsystem 174 may include one or more of the embodiments described herein for unified hardware acceleration of hash functions.

Security credentials 180 may include one or more values employed by security subsystem 174 as inputs to its performance of encryption of data 130 and/or of decryption of encrypted data 134 as part of performing conversions there between during normal operation of processing device 105. More specifically, security credentials 180 may include any of a variety of types of security credentials, including and not limited to public and/or private keys, seeds for generating random numbers, instructions to generate random numbers, certificates, signatures, ciphers, and/or the like. Security subsystem 174 may be provided with access to security credentials 180 during initialization of the processing device 105.

Figure 11:
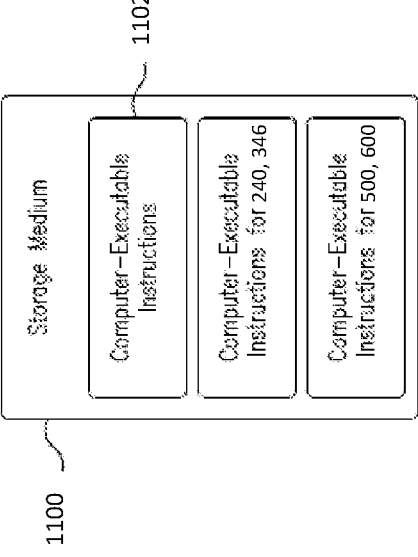
FIG. 11 illustrates an exemplary embodiment of a storage medium of an electroporation delivery system in accordance with the present disclosure.

FIG. 11 illustrates an example of a storage medium 1100. Storage medium 1100 may comprise an article of manufacture. In some examples, storage medium 1100 may include any non-transitory computer readable medium or machine readable medium, such as an optical, magnetic or semiconductor storage. Storage medium 1100 may store various types of computer executable instructions, such as instructions 1102, which may correspond to any embodiment described herein, or to implement the algorithms described herein and illustrated in flow charts 240, 252, 346, 358, 500, and 600. Examples of a computer readable or machine readable storage medium may include any tangible media capable of storing electronic data, including volatile memory or non-volatile memory, removable or non-removable memory, erasable or non-erasable memory, writeable or re-writeable memory, and so forth. Examples of computer executable instructions may include any suitable type of code, such as source code, compiled code, interpreted code, executable code, static code, dynamic code, object-oriented code, visual code, and the like. The examples are not limited in this context.

Figure 12:
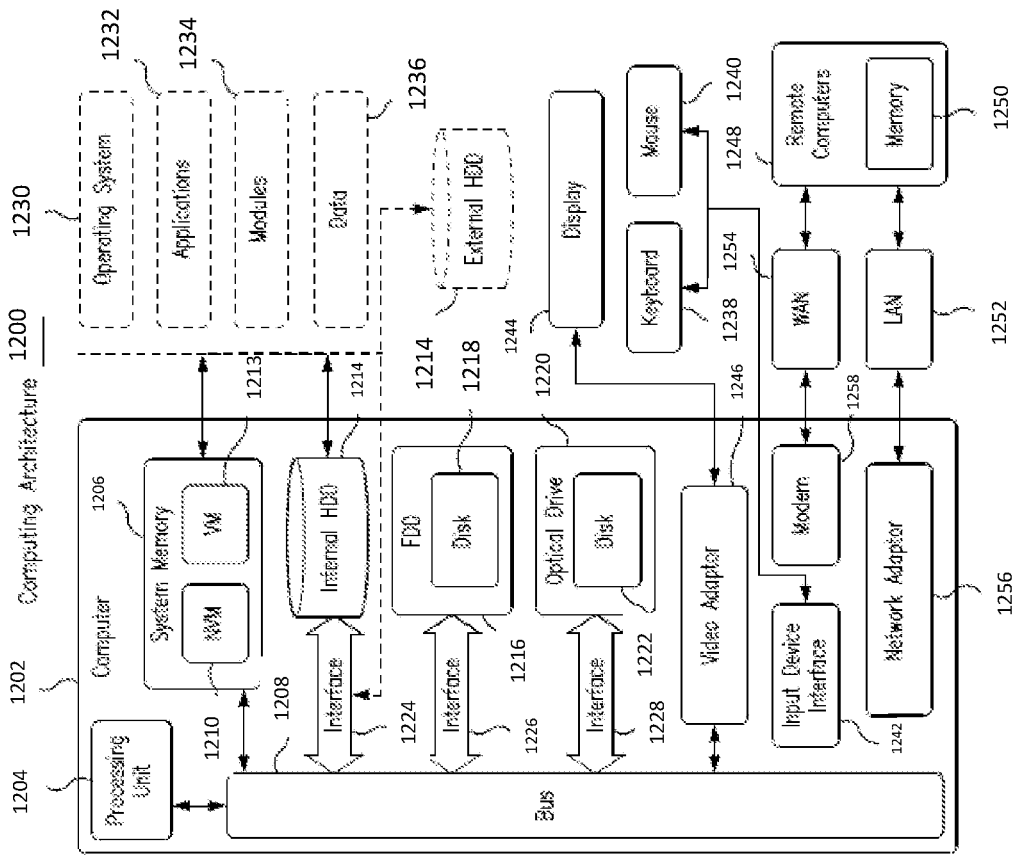
FIG. 12 illustrates an exemplary embodiment of a computing architecture of an electroporation delivery system in accordance with the present disclosure.

FIG. 12 illustrates an embodiment of an exemplary computing architecture 1200 suitable for implementing various embodiments as previously described. In one embodiment, the computing architecture 1200 may comprise or be implemented as part of an electronic device. Examples of an electronic device may include those described herein, such as electroporation delivery system 905 of FIG. 9 and processing device 105 of FIG. 10. The embodiments are not limited in this context.

As used in this application, the terms "system" and "component" are intended to refer to a computer-related entity, either hardware, a combination of hardware and software, software, or software in execution, examples of which are provided by the exemplary computing architecture 1200. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1200 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1200.

As shown in FIG. 12, the computing architecture 1200 comprises a processing unit 1204, a system memory 1206 and a system bus 1208. The processing unit 1204 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1204. For example, the unified hardware acceleration for hash functions described herein may be performed by processing unit 1204 in some embodiments.

The system bus 1208 provides an interface for system components including, but not limited to, the system memory 1206 to the processing unit 1204. The system bus 1208 can be any of several types of bus structure that may further interconnect to a memory bus (with or without a memory controller), a peripheral bus, and a local bus using any of a variety of commercially available bus architectures. Interface adapters may connect to the system bus 1208 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 1200 may comprise or implement various articles of manufacture. An article of manufacture may comprise a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

The system memory 1206 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 12, the system memory 1006 can include non-volatile memory 1210 and/or volatile memory 1213. A basic input/output system (BIOS) can be stored in the non-volatile memory 1210.

The computer 1202 may include various types of computer-readable storage media in the form of one or more lower speed memory units, including an internal (or external) hard disk drive (HDD) 1214, a magnetic floppy disk drive (FDD) 1216 to read from or write to a removable magnetic disk 1218, and an optical disk drive 1220 to read from or write to a removable optical disk 1222 (e.g., a CD-ROM, DVD, or Blu-ray). The HDD 1214, FDD 1216 and optical disk drive 1220 can be connected to the system bus 1208 by a HDD interface 1224, an FDD interface 1226 and an optical drive interface 1228, respectively. The HDD interface 1224 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, a number of program modules can be stored in the drives and memory 1210, 1213, including an operating system 1230, one or more application programs 1232, other program modules 1234, and program data 1236. In one embodiment, the one or more application programs 1232, other program modules 1234, and program data 1236 can include, for example, the various applications and/or components to implement the disclosed embodiments.

A user can enter commands and information into the computer 1202 through one or more wire/wireless input devices, for example, a keyboard 1238 and a pointing device, such as a mouse 1240. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1204 through an input device interface 1242 that is coupled to the system bus 1208, but can be connected by other interfaces such as a parallel port, IEEE 1394 serial port, a game port, a USB port, an IR interface, and so forth.

A display 1244 is also connected to the system bus 1208 via an interface, such as a video adaptor 1246. The display 1244 may be internal or external to the computer 1202. In addition to the display 1244, a computer typically includes other peripheral output devices, such as speakers, printers, and so forth.

The computer 1202 may operate in a networked environment using logical connections via wire and/or wireless communications to one or more remote computers, such as a remote computer 1248. The remote computer 1248 can be a workstation, a server computer, a router, a personal computer, portable computer, microprocessor-based entertainment appliance, a peer device or other common network node, and typically includes many or all of the elements described relative to the computer 1202, although, for purposes of brevity, only a memory/storage device 1250 is illustrated. The logical connections depicted include wire/wireless connectivity to a local area network (LAN) 1252 and/or larger networks, for example, a wide area network (WAN) 1254. Such LAN and WAN networking environments are commonplace in offices and companies, and facilitate enterprise-wide computer networks, such as intranets, all of which may connect to a global communications network, for example, the Internet.

When used in a LAN networking environment, the computer 1202 is connected to the LAN 1252 through a wire and/or wireless communication network interface or adaptor 1256. The adaptor 1256 can facilitate wire and/or wireless communications to the LAN 1252, which may also include a wireless access point disposed thereon for communicating with the wireless functionality of the adaptor 1256.

When used in a WAN networking environment, the computer 1202 can include a modem 1258, or is connected to a communications server on the WAN 1254, or has other means for establishing communications over the WAN 1254, such as by way of the Internet. The modem 1258, which can be internal or external and a wire and/or wireless device, connects to the system bus 1208 via the input device interface 1242. In a networked environment, program modules depicted relative to the computer 1202, or portions thereof, can be stored in the remote memory/storage device 1250. It will be appreciated that the network connections shown are exemplary and other means of establishing a communications link between the computers can be used.

The computer 1202 is operable to communicate with wire and wireless devices or entities using the IEEE 802 family of standards, such as wireless devices operatively disposed in wireless communication (e.g., IEEE 802.11 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

One or more aspects of at least one embodiment described herein may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An electroporation delivery system, comprising:
an electrocardiogram monitor operatively connected to a processing device and a memory;
one or more sensors operatively connected to the electrocardiogram monitor for measuring an electrocardiogram of a heart of a patient; and
one or more electrodes configured to deliver treatment in, at, or near the patient's heart, the one or more electrodes operatively connected to a pulse delivery mechanism,
wherein, in order to account for irregular heartbeats of the patient's heart, the electroporation delivery system is configured to determine whether an electroporation pulse is to be delivered from the pulse delivery mechanism to the patient using a rolling average of the electrocardiogram.

2. The electroporation delivery system according to claim 1, wherein the processing device is configured to execute the following steps:
measuring and averaging approximately 30 initial heartbeat durations of the patient's heart;
calculating the rolling average by averaging a series of four heartbeat durations;
comparing the rolling average to the averaged initial heartbeat durations including a standard deviation; and
if the rolling average is equal to the average initial heartbeat durations within the standard deviation, delivering the electroporation pulse during a fifth heartbeat duration following the averaged series of four heartbeat durations, and if the rolling average is not equal to the average initial heartbeat durations within the standard deviation, not delivering the electroporation pulse during the fifth heartbeat duration following the averaged series of four heartbeat durations.

3. The electroporation delivery system according to claim 1, wherein the processing device is configured to execute the following steps:

calculating a rolling average by averaging a series of four heartbeat durations;

setting the rolling average to a heartbeat average including a standard deviation; and comparing the rolling average to a fifth heartbeat duration following the averaged series of four heartbeat durations, wherein if the fifth heartbeat duration following the averaged series of four heartbeat durations is equal to the rolling average within the standard deviation, delivering an electroporation pulse during a sixth heartbeat duration following the fifth heartbeat duration, and if the fifth heartbeat duration following the averaged series of the four heartbeat durations is not equal to the rolling average within the standard deviation, not delivering the electroporation pulse during the sixth heartbeat duration following the fifth heartbeat duration.

4. The electroporation delivery system according to claim 3, wherein delivery of the electroporation pulse during the sixth heartbeat duration occurs at a time determined by the averaged series of four heartbeat durations divided by two after a Q wave of a QRS complex of the sixth heartbeat duration.

5. The electroporation delivery system according to claim 1, wherein the processing device is configured to execute the following steps:

measuring and averaging approximately 30 initial R wave amplitudes in a QRS complex of the patient's heart;

calculating a rolling average by averaging a series of four R wave amplitudes; and comparing the rolling average to the average initial R wave amplitudes including a standard deviation, wherein if the rolling average is equal to the average initial R wave amplitudes within the standard deviation, delivering the electroporation pulse during a fifth heartbeat duration following the averaged series of four R wave amplitudes, and if the rolling average is not equal to the average initial R wave amplitudes within the standard deviation, not delivering the electroporation pulse during the fifth heartbeat duration following the averaged series of four R wave amplitudes.

6. The electroporation delivery system according to claim 1, wherein the processing device is configured to execute the following steps:

calculating a rolling average by averaging a series of four R wave amplitudes in a QRS complex of the patient's heart;

setting the rolling average to the averaged R wave amplitudes including a standard deviation; and comparing the rolling average to a fifth R wave amplitude of a fifth heartbeat duration following the averaged series of four R wave amplitudes, wherein if the fifth R wave amplitude following the averaged series of four R wave amplitudes is equal to the rolling average within the standard deviation, delivering the electroporation pulse during a sixth heartbeat duration following the fifth R wave amplitude, and if the fifth R wave amplitude following the averaged series of the four R wave amplitudes is not equal to the rolling average within the standard deviation, not delivering the electroporation pulse during the sixth heartbeat duration following the fifth R wave amplitude.

7. The electroporation delivery system according to claim 1, further comprising one or more signal filters for extracting at least one of an R wave and a T wave of a QRS complex;

wherein the electroporation pulse is deliverable in response to a positive value of the R wave and a negative value of the T wave output from the one or more filters;

wherein the electroporation pulse is not deliverable in response to the positive value of the R wave and a positive value of the T wave output from the one or more filters; and wherein the electroporation pulse is deliverable in response to the R wave being within 70 ms and the negative value of the T wave output from the one or more filters.

8. The electroporation delivery system according to claim 1, wherein pacing of the patient's heart is adjustable for electroporation pulse delivery by induced pacing, including the following steps:

pacing a portion of the patient's heart;

detecting an evoked potential, wherein if no evoked potential is detected, the pacing of the portion of the patient's heart is continued and no electroporation pulse is delivered, and:

in response to detecting evoked potential, determining if the detection occurs during a vulnerable period of a T wave;

wherein in response to the detection occurring during the vulnerable period of the T wave, the pacing of the portion of the patient's heart is continued and no electroporation pulse is delivered; and wherein in response to the detection not occurring during the vulnerable period of the T wave, delivering the electroporation pulse.

9. The electroporation delivery system according to claim 1, wherein pacing of the patient's heart is adjustable for electroporation pulse delivery by continuous pacing, including the following steps:

(a) sending a continuous pacing signal to the patient's heart to maintain the heart in a contracted state;

(b) during the continuous pacing, delivering one or more electroporation pulses; and (c) monitoring heart rhythms of the patient for irregularities, wherein in response to detecting an irregularity, pacing the patient's heart to a normal rhythm; and wherein in response to detecting a regular heartbeat, repeating steps (a), (b), and (c) if additional treatment is needed.

10. The electroporation delivery system according to claim 1, wherein electroporation pulse delivery is paused for monitoring the electrocardiogram for regular heart rhythms.

11. The electroporation delivery system according to claim 1, wherein an electroporation pulse shape is at least one of square-shaped and defibrillation-like shaped, and wherein the electroporation pulse shape is at least one of monopolar and bipolar.

12. The electroporation delivery system according to claim 1, wherein the electroporation delivery system is operational for treating at least one of atrial fibrillation and cancer disposed in, at, or near the heart.

13. A method for delivering an electroporation pulse by an electroporation delivery system for treatment in, at, or near a patient's heart, comprising:

measuring electrical activity QRS complex of the patient's heart using an electrocardiogram monitor and one or more sensors operatively connected to a processing device and a memory;

calculating, by the processing device, a rolling average by averaging a series of four heartbeat parameters; and delivering, based on the rolling average, the electroporation pulse by one or more electrodes operatively connected to a pulse delivery mechanism of the electroporation delivery system.

14. The method according to claim 13, wherein the delivering, based on the rolling average, the electroporation pulse comprises:

measuring and averaging approximately 30 initial heartbeat parameters of a patient's heart; and including a standard deviation to the average initial heartbeat parameters.

15. The method according to claim 13, wherein the delivering, based on the rolling average, the electroporation pulse comprises using a fifth heartbeat parameter following the averaged series of four heartbeat parameters, and the rolling average is set to a heartbeat average including a standard deviation.

16. The method according to claim 15, further comprising:

delivering the electroporation pulse during a fifth heartbeat duration following the averaged series of four heartbeat parameters; and not delivering the electroporation pulse during the fifth heartbeat duration following the averaged series of four heartbeat parameters in response to the rolling average not equaling a determined value.

17. The method according to claim 15, further comprising:

delivering the electroporation pulse during a sixth heartbeat duration following a fifth heartbeat duration; and not delivering the electroporation pulse during the sixth heartbeat duration following the fifth heartbeat duration in response to the fifth heartbeat parameter not equaling the rolling average within the standard deviation.

18. The method according to claim 13, wherein a heartbeat parameter is at least one of a heartbeat duration and an R wave amplitude.

19. The method according to claim 13, further comprising adjusting a pace of the patient's heart at least one of before, during, and after delivering the electroporation pulse.

20. A system for delivering an electroporation pulse by an electroporation delivery system for treatment in, at, or near a patient's heart, the system being configured to execute the following steps:

measuring electrical activity QRS complex of the patient's heart using an electrocardiogram monitor and one or more sensors operatively connected to a processing device and a memory;

calculating, by the processing device, a rolling average by averaging a series of four heartbeat parameters; and delivering, based on the rolling average, the electroporation pulse by one or more electrodes operatively connected to a pulse delivery mechanism of the electroporation delivery system.

* * * * *